United States Patent
Hayashi et al.

(10) Patent No.: US 7,032,433 B2
(45) Date of Patent: Apr. 25, 2006

(54) SENSOR, SENSOR PRODUCING METHOD, AND ASSEMBLY OF SEPARATOR AND URGING MEMBER

(75) Inventors: Takahiro Hayashi, Kani (JP); Masataka Taguchi, Kakamigahara (JP); Yasuhiro Fujita, Gifu (JP); Yoshiaki Matsubara, Nagoya (JP); Hitoshi Iimi, Okazaki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/506,139

(22) PCT Filed: Jul. 10, 2003

(86) PCT No.: PCT/JP03/08787

§ 371 (c)(1),
(2), (4) Date: Sep. 1, 2004

(87) PCT Pub. No.: WO2004/010130

PCT Pub. Date: Jan. 29, 2004

(65) Prior Publication Data

US 2005/0145013 A1     Jul. 7, 2005

(30) Foreign Application Priority Data

Jul. 19, 2002   (JP) .............................. 2002-211687

(51) Int. Cl.
    *G01N 27/409*    (2006.01)
    *G01N 37/00*    (2006.01)

(52) U.S. Cl. .................... 73/31.05; 73/23.31; 204/424; 29/592.1; 29/595

(58) Field of Classification Search ................ 73/23.31, 73/31.05; 204/424, 426, 431; 29/592.1, 29/595

See application file for complete search history.

(56) References Cited

U.S. PATENT DOCUMENTS 5,573,650 A    11/1996   Fukaya et al.

(Continued)

FOREIGN PATENT DOCUMENTS

JP      64-15159 U     1/1989

(Continued)

OTHER PUBLICATIONS

International Search Report for PCT/JP03/08787 dated Aug. 26, 2003.

*Primary Examiner*—Daniel S. Larkin
(74) *Attorney, Agent, or Firm*—Sughrue Mion, PLLC

(57) ABSTRACT

It is an object of the invention to provide a sensor which is highly reliable, and a method or producing a sensor which is highly reliable, and which can be easily produced. A method of producing a sensor in which bending of a heater and the like hardly occur is provided.

In the invention, an oxygen sensor (1) has: an oxygen sensor element (2); a metal shell (3); first and second sensor terminal metal parts (11), (12); a heater (15); heater terminal metal parts (16), (17); a metal outer tube (21); and a separator (31) which is housed inside the metal outer tube (21), in which the terminal metal part (11) and the like and the heater (15) are held, and which provides insulation between the terminal metal part (11) and the like. An outer-tube butting face (34*a*) is formed in a flange portion (34) of the separator (31). In the metal outer tube (21), a flange butting face (24*b*) which butts against the outer-tube butting face (34*a*) is formed. Both of the outer-tube butting face (34*a*) and the flange butting face (24*b*) form an inclined face which is more radially outward positioned as further advancing toward the tip end. The separator (31) is pressed toward the rear end. The pressing is conducted by deforming the metal outer tube (21), and deforming a pressing metal part (41) which is placed around a tip end side portion (33) of the separator (31).

18 Claims, 14 Drawing Sheets

U.S. PATENT DOCUMENTS

| | | |
|---|---|---|
| 6,360,581 B1 | 3/2002 | Murase et al. |
| 2001/0035045 A1 | 11/2001 | Hibino et al. ............ 73/31.05 |
| 2002/0038793 A1 | 4/2002 | Yamada et al. |

FOREIGN PATENT DOCUMENTS

| | | |
|---|---|---|
| JP | 6-331595 A | 12/1994 |
| JP | 2001-147213 A | 5/2001 |
| JP | 2001-153833 A | 6/2001 |
| JP | 2001-311713 A | 11/2001 |
| JP | 2002-39986 A | 2/2002 |
| JP | 2003-194764 A | 7/2003 |

SECTION ALONG A-A

SECTION ALONG B-B

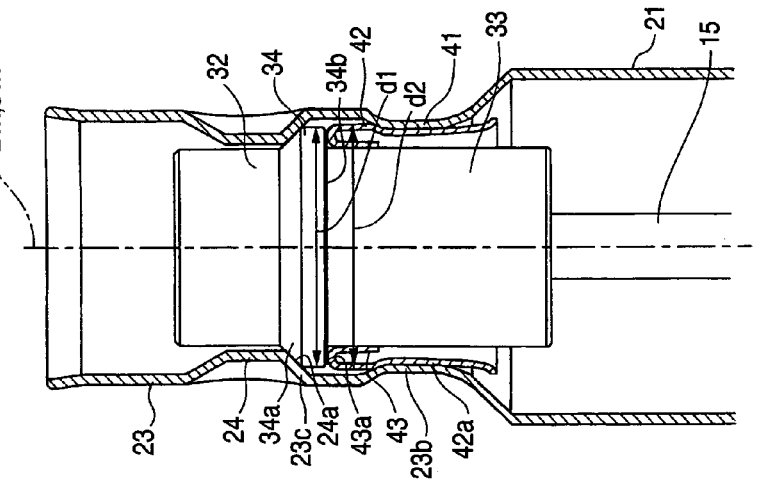
FIG. 12 (a) BEFORE DEFORMATION
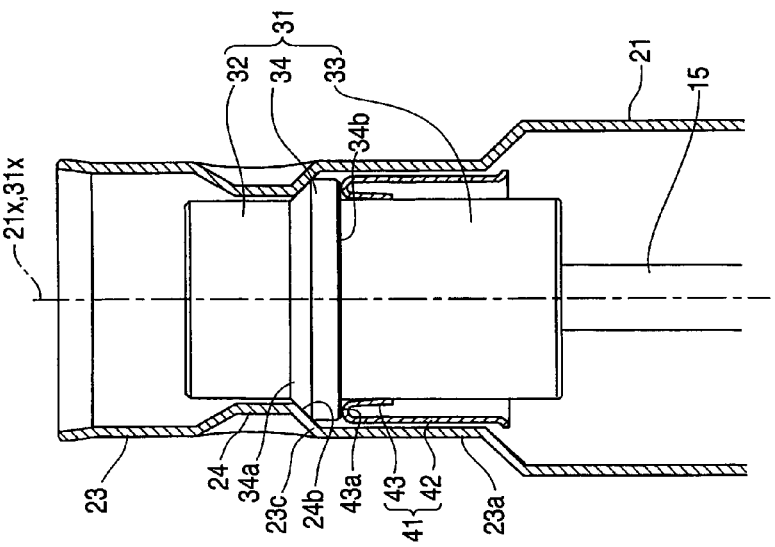
FIG. 12 (b) AFTER DEFORMATION

SENSOR, SENSOR PRODUCING METHOD, AND ASSEMBLY OF SEPARATOR AND URGING MEMBER

TECHNICAL FIELD

The present invention relates to a sensor in which a sensor element is attached to a metal shell or the like, and also to a method of producing a sensor.

BACKGROUND ART

In an internal combustion engine, for example, it is known that a technique in which the oxygen concentration in exhaust gas, the air-fuel ratio state, and the like are detected and a combustion control is conducted on the basis of detected values is very effective for energy saving, purification of exhaust gas, etc. As a sensor for detecting the oxygen concentration or the like in exhaust gas (to-be-measured gas), known is a gas sensor in which a detecting element made of a solid electrolyte such as zirconia is used. Various improvements have been applied on such a gas sensor.

For example, JP-A-2001-147213 discloses a gas sensor 1001 shown in FIG. 1. The gas sensor 1001 is an oxygen sensor which is to be used in an internal combustion engine for an automobile, and has: a detecting element 1010 having a gas-exposed portion 1011 which is to be in contact with to-be-measured gas; a metal shell 1004 which holds the detecting element 1010 in the state where the gas-exposed portion 1011 is exposed; and a protective cover 1002 which is disposed from the metal shell 1004 to cover the gas-exposed portion 1011 of the detecting element 1010. The gas sensor further has: two lead terminals 1071, 1072 which are electrically connected to the detecting element 1010; plural lead wires 1081, 1091 which are to be electrically connected to them, respectively; connectors 1075, 1076 through which the lead terminals 1071, 1072 are connected to the lead wires 1081, 1091; an electrically insulative insulating member 1005 which provides insulation between the connectors 1075, 1076, and a first metal cover 1003 in which the insulating member 1005 is housed. A heater 1015 which is placed inside the detecting element 1010 in order to heat the detecting element 1010 is connected to the outside through a lead wire 1171 and another lead wire which is not shown.

The insulating member 1005 has: a main portion 1051 which houses a part of the lead wires 1081, 1091, 1171, the connectors 1075, 1076, and the like; and a flange portion 1052 which is larger in diameter than the main portion 1051. The first metal cover 1003 has: a small-diameter portion 1031 having an inner diameter which is larger than the outer diameter of the main portion 1051 of the insulating member 1005, and which is smaller than the outer diameter of the flange portion 1052; a large-diameter portion 1032 having an inner diameter which is larger than the outer diameter of the flange portion 1052; and a step portion 1033 which connects the small-diameter portion 1031 with the large-diameter portion 1032.

In the insulating member 1005, one face (the upper face in the figure) 1521 of the flange portion 1052 butts against the step portion 1033, and the other face (the lower face in the figure) 1522 of the flange portion 1052 is pressed and fixed by an elastic member 1006 which is pressingly inserted into the large-diameter portion 1032. Namely, the insulating member 1005 is fixed with being clamped between the elastic member 1006 and the step portion 1033 of the first metal cover 1003.

According to the configuration, unlike a conventional gas sensor, the gas sensor 1001 is not required to have a structure in which an insulating member is fixed by combining plural covers. Since the insulating member 1005 is fixed by using the elastic member 1006, the joining position between the first metal cover 1003 and the metal shell 1004, and the like are not affected even when the size of the insulating member 1005 is dispersed. Consequently, there are advantages such as that the dimension accuracy of the total length of the gas sensor 1001 can be improved.

In the gas sensor 1001, as described above, the insulating member 1005 is fixed by causing the face 1521 of the flange portion 1052 of the insulating member 1005 which face is substantially perpendicular to the axial direction (the vertical direction in FIG. 1) to butt against the step portion 1033 of the first metal cover 1003 which step portion is similarly perpendicular to the axial direction. However, the outer diameter of the flange portion 1052 of the insulating member 1005 is smaller than the inner diameter of the large-diameter portion 1032 of the first metal cover 1003. Consequently, there is the possibility that the insulating member 1005 is fixed to the first metal cover 1003 in an inadequately misaligned state where the axis of the first metal cover 1003 fails to coincide with that of the insulating member 1005. As a result, also a part of the lead wires 1081, 1091, 1171 held in the insulating member 1005, the connectors 1075, 1076, and the like are held with being deviated from their original held positions, so that unwanted stresses are applied to the lead wires 1081, 1091, 1171, the connectors 1075, 1076, and the like. Consequently, there is the possibility that defects including destruction such as bending of the detecting element 1010 or the heater 1015, and breakage or disconnection of the lead wire 1081, the connector 1075, and the like occur.

The gas sensor 1001 is produced in the following manner. First, the insulating member 1005 in a state where the lead wire 1081, the connector 1075, and the like are not housed in the member is previously fixed to the inside of the first metal cover 1003 by using the elastic member 1006. Thereafter, the lead wire 1081, the connector 1075, and the like are housed in the insulating member 1005. The heater 1015 is then inserted into the detecting element 1010, and the first metal cover 1003 is fixed to the metal shell 1004.

However, the work of housing the lead wire 1081, the connector 1075, and the like in the insulating member 1005 in the state where the insulating member 1005 is fixed to the inside of the first metal cover 1003 is cumbersome. It is difficult to house the lead wire 1081, the connector 1075, and the like at adequate positions in the insulating member 1005. When these components fail to be housed at adequate positions, moreover, unwanted stresses are applied to the lead wires 1081, 1091, 1171, the connectors 1075, 1076, and the like in the same manner as the above-mentioned case where positional deviation occurs, and a defect such as breakage or disconnection may occur.

It may be contemplated that, conversely, the lead wire 1081, the connector 1075, and the like are previously housed at adequate positions in the insulating member 1005, and the insulating member 1005 is then fixed to the inside of the first metal cover 1003. However, the lead wire 1081, the connector 1075, and the like are already housed in the insulating member 1005. As compared with the case where these components do not exist, therefore, it is difficult to pressingly insert the elastic member 1006 into the first metal cover 1003, and the work of fixing the insulating member 1005 to the inside of the first metal cover 1003 is cumbersome.

The gas sensor 1001 is produced in the following manner. As described above, first, the insulating member 1005 in which the lead wire 1081 and the like are not housed is fixed to the inside of the first metal cover 1003 by using the elastic member 1006. Thereafter, the lead wire 1081, the connector 1075, and the like are housed in the insulating member 1005. The heater 1015 is then inserted into the detecting element 1010, and the first metal cover 1003 is fixed to the metal shell 1004. Depending on the housed state of the lead wire 1171 and the like housed in the insulating member 1005, there is possibly a case in which the state where the heater 1015 to be connected to them is inclined with respect to the axis of the insulating member 1005 is most stable.

In the production method, however, the heater 1015 is inserted into the detecting element 1010 in the state where the insulating member 1005 is fixed to the inside of the first metal cover 1003. Therefore, the inclination of the heater 1015 is compulsively changed by the insertion. As a result, unwanted stresses are applied to the heater 1015, the lead terminals thereof, the lead wire 1171, and the like, thereby causing the possibility that a defect such as breakage, disconnection, or bending of the heater occurs.

The invention has been conducted in view of the problems. It is an object of the invention to provide a sensor that has a metal outer tube in which terminal members such as a connector are housed and a separator for providing insulation between the terminal members, and the like from one another is housed and fixed, in a manner similar to the insulating member and the first metal cover described above, and that is highly reliable, and also a method of producing a sensor that is highly reliable, and that can be easily produced. It is another object of the invention to provide a method of producing a sensor in which bending of a heater and the like hardly occur. It is a further object of the invention to provide an assembly of a separator and a pressing member that is suitable for production of a sensor.

DISCLOSURE OF THE INVENTION

The solving means is a sensor having: a sensor element; a metal shell which holds the sensor element; one or more sensor terminal members which are electrically connected to the sensor element, and which elongate from the sensor element toward a rear end; a metal outer tube which is connected to the metal shell at a tip end portion of the metal outer tube itself; and an electrically insulative separator which is housed inside the metal outer tube, in which the sensor terminal members are positioned, and which provides at least one of insulation between the sensor terminal members, and insulation between the sensor terminal members and the metal outer tube, wherein the separator has: a rear end side portion; and a flange portion which is positioned on a tip end side with respect to the rear end side portion, and which is larger in diameter than the rear end side portion, the metal outer tube has a step portion or an inner projection which butts against the flange portion of the separator, at least one of an outer-tube butting portion of the flange portion of the separator, and a flange butting portion of the step portion or the inner projection of the metal outer tube forms an inclined face which is more radially outward positioned as further advancing toward the tip end, the outer-tube butting portion butting against the step portion or the inner projection of the metal outer tube, the flange butting portion butting against the outer-tube butting portion of the flange portion of the separator, and the separator is held by the metal outer tube in a state where the separator is pressed toward the rear end.

In the sensor of the invention, the flange portion of the separator has the outer-tube butting portion which butts against the step portion or the inner projection of the metal outer tube, and the step portion or the inner projection of the metal outer tube has the flange butting portion which butts against the outer-tube butting portion of the separator. At least one of the outer-tube butting portion and the flange butting portion forms the inclined face which is more radially outward positioned as further advancing toward the tip end. Moreover, the separator is pressed toward the rear end. Namely, the separator is pressed in a direction along which the outer-tube butting portion and the flange butting portion approach each other. Furthermore, in this state, the separator is held inside the metal outer tube.

Even in the case where, during a process of assembling the sensor, the axis of the separator is set to be deviated from that of the metal outer tube, when the separator is pressed toward the rear end, the separator moves along the inclined face of at least one of the outer-tube butting portion and the flange butting portion so as to reduce the deviation between the axes. Therefore, the position of the separator with respect to the metal outer tube can be adequately determined, and hence also the positions of the sensor terminal members placed in the separator can be correctly determined. As a result, in the sensor, a defect such as destruction of the sensor element or breakage of the sensor terminal members due to application of stress on the sensor terminal members themselves or between the sensor terminal members and the sensor element because of positional or postural deviation of the sensor terminal members can be prevented from occurring, the separator can be stably fixed inside the metal outer tube, and the reliability is high.

As described above, at least one of the outer-tube butting portion and the flange butting portion is required to form the inclined face which is more radially outward positioned as further advancing toward the tip end. In the case where the outer-tube butting portion forms a tapered face in which the diameter is made larger as further advancing toward the tip end, for example, the flange butting portion may be a tapered face which butts against the tapered face in a surface or point contact state, or have another form. In the case where the flange butting portion forms a tapered face in which the diameter is made larger as further advancing toward the tip end, the outer-tube butting portion may be a tapered face which butts against the tapered face in a surface or point contact state, or have another form.

The other solving means is a sensor having: a sensor element; a metal shell which holds the sensor element; one or more sensor terminal members which are electrically connected to the sensor element, and which elongate from the sensor element toward a rear end; a metal outer tube which is connected to the metal shell at a tip end portion of the metal outer tube itself; and an electrically insulative separator which is housed inside the metal outer tube, in which the sensor terminal members are positioned, and which provides at least one of insulation between the sensor terminal members, and insulation between the sensor terminal members and the metal outer tube, wherein the separator has: a rear end side portion; and a flange portion which is positioned on a tip end side with respect to the rear end side portion, and which is larger in diameter than the rear end side portion, the metal outer tube has a step portion or an inner projection which butts against the flange portion of the separator, both of an outer-tube butting face of the flange portion of the separator, and a flange butting face of the step portion or the inner projection of the metal outer tube form an inclined face which is more radially outward positioned as further advancing toward the tip end, the outer-tube butting face butting against the step portion or the inner projection of the metal outer tube and facing the rear end side, the flange butting face butting against the outer-tube butting face of the flange portion of the separator, and the separator is held by the metal outer tube in a state where the separator is pressed toward the rear end.

In the sensor of the invention, the flange portion of the separator has the outer-tube butting face forming an inclined face which faces the rear end side, which butts against the step portion or the inner projection of the metal outer tube, and which is more radially outward positioned as further advancing toward the tip end, for example, an a tapered face in which the diameter is made larger as further advancing toward the tip end. Furthermore, also the step portion or the inner projection of the metal outer tube has the flange butting face forming an inclined face which faces the tip end side, which butts against the outer-tube butting face of the separator, and which is more radially outward positioned as further advancing toward the tip end, for example, a tapered face in which the diameter is made larger as further advancing toward the tip end. Moreover, the separator is pressed toward the rear end. Namely, the separator is pressed in a direction along which the outer-tube butting face and the flange butting face approach each other. Furthermore, the separator is held inside the metal outer tube in this state.

Even in the case where, during a process of assembling the sensor, the axis of the separator is set to be deviated from that of the metal outer tube, when the separator is pressed toward the rear end, the separator moves along the inclined faces of the separator and the metal outer tube so as to reduce the deviation between the axes. Therefore, the position of the separator with respect to the metal outer tube can be adequately determined, and hence also the positions of the sensor terminal members placed in the separator can be correctly determined. As a result, in the sensor, a defect such as destruction of the sensor element or breakage of the sensor terminal members due to application of stress on the sensor terminal members themselves or between the sensor terminal members and the sensor element because of positional or postural deviation of the sensor terminal members can be prevented from occurring, the separator can be stably fixed inside the metal outer tube, and the reliability is high.

In the sensor described above, it is requested to have one or more sensor terminal members which are electrically connected to the sensor element. An example of the case of one sensor terminal member is a case where one of sensor signals is output through the sensor terminal member, and the other sensor signal is set as the ground potential through the metal shell and the metal outer tube. In this case, insulation between the sensor terminal member and the metal outer tube is provided by the separator. An example of the case of plural sensor terminal members is a case where sensor signals of + and − are output. In this case, insulation between the sensor terminal members is provided by the separator.

Any mechanism which can press the separator toward the rear end may be employed in order to press the separator. For example, an annular metal plate in which nail portions protruding in the form of a gear are formed in the outer periphery is pressingly inserted into the metal outer tube, the nail portions are pressingly contacted with the inner wall of the metal outer tube, and the annular body portion butts against the tip end side face of the flange portion of the separator, whereby the separator can be pressed toward the rear end.

As the sensor, any sensor having a sensor element, a metal shell, a metal outer tube, a separator, and the like can be used. For example, a gas sensor such as an oxygen sensor, a NOx sensor, or an HC sensor, a temperature sensor, and other sensors can be used.

Preferably, the sensor is configured so that the flange portion of the separator has a tip end side face facing the tip end side, and the sensor comprises a pressing member which is held inside the metal outer tube, and which butts against the tip end side face of the flange portion to press the separator toward the rear end, the pressing member being in point contact with the tip end side face as seen in a radial direction.

Depending on the attachment position and manner of the sensor terminal members, and also on the arrangement of lead wires connected to the sensor terminal members, the shape of a grommet which is fitted into a rear end opening of the metal outer tube in order to make the interior of the metal outer tube airtight, the manner of a airtight seal such as caulking of the metal outer tube around the grommet, and the like, various forces act on the separator through the sensor terminal members and the lead wires during a process of assembling the sensor, and try to change the posture of the separator.

When the separator is firmly fixed to the metal outer tube, however, the posture of the separator is not changed. Therefore, stresses are applied to the sensor terminal members, the sensor element, and the lead wires, and there arises the possibility that a defect such as that the sensor terminal members or the lead wires are broken occurs.

By contrast, in the sensor of the invention, the pressing member has, for example, an annular shape, or an annular shape in which various portions are interrupted, and is in point contact with the tip end side face as seen in a radial direction. As compared with the case where, although the separator is similarly pressed toward the rear end, the butting portion has a width and annularly extends, therefore, the posture of the separator (for example, deviation of the axis of the separator with respect to that of the metal outer tube, inclination of the axis, and rotation) is changed in a relatively easy manner during a process of assembling the sensor. Consequently, stresses are hardly applied to the sensor terminal members, the lead wires, and the like during a process of assembling the sensor. As a result, the resulting sensor is a sensor in which a defect such as crack of the sensor element, or breakage of the sensor terminal members or the lead wires can be prevented from occurring, and which is highly reliable.

Preferably, any of the above-described sensors is configured as a sensor in which the sensor element is a cylindrical gas sensor element in which a tip end side is closed, the sensor has: a rod heater which is inserted into a bottomed hole of the gas sensor element; and one or more heater terminal members which are electrically connected to the heater, and the separator is a separator which provides insulation between the sensor terminal members and the heater terminal members.

The sensor of the invention uses a cylindrical gas sensor element in which a tip end side is closed, as the sensor element, has a rod heater which is inserted into a bottomed hole of the gas sensor element, and heater terminal members which are electrically connected to the heater, and the separator provides insulation between the sensor terminal members, and also insulation between the heater terminal members. In a sensor (gas sensor) which has a heater and heater terminal members in addition to a sensor element as described above, the position of the separator in the metal outer tube is affected also by the arrangement and posture of the heater terminal members, the heater, etc., and hence the axis of the separator tends to be set to be deviated from that of the metal outer tube during a process of assembling the sensor.

By contrast, in the sensor of the invention, as described above, the flange portion of the separator comprises the outer-tube butting face forming an inclined face which is more radially outward positioned as further advancing toward the tip end, and also the step portion or the inner projection of the metal outer tube has the flange butting face forming an inclined face which is more radially outward positioned as further advancing toward the tip end. Moreover, the separator is pressed toward the rear end. In the same manner as described above, therefore, the position of the separator with respect to the metal outer tube can be adequately determined, and hence also the positions of the sensor terminal members and the heater terminal members held by the separator can be correctly determined. As a result, in the sensor, a defect such as destruction of the sensor element, breakage of the sensor terminal members, destruction (bending) of the heater, or breakage of the heater terminal members due to application of stress on the sensor terminal members themselves, between the sensor terminal members and the sensor element, the heater terminal members themselves, or between the heater terminal members and the heater because of positional or postural deviation of the sensor terminal members and the heater terminal members can be prevented from occurring, and the reliability is high.

The other solving means is a method of producing a sensor, the sensor having: a sensor element; a metal shell which holds the sensor element; one or more sensor terminal members which are electrically connected to the sensor element, and which elongate from the sensor element toward a rear end; a metal outer tube which is connected to the metal shell at a tip end portion of the metal outer tube itself; and an electrically insulative separator which is housed inside the metal outer tube, the separator including: a rear end side portion which is positioned on a side of the rear end; a tip end side portion which is positioned on a side of a tip end; and a flange portion which is positioned at a middle between the rear end side portion and the tip end side portion, which is larger in diameter than the rear end side portion and the tip end side portion, and which has a tip end side face facing the tip end side between the flange portion and the tip end side portion, and a rear end side face facing the rear end side between the flange portion and the rear end side portion, the sensor terminal members being positioned inside, the separator providing at least one of insulation between the sensor terminal members, and insulation between the sensor terminal members and the metal outer tube, the metal outer tube having a step portion or an inner projection which butts against the rear end side of the flange portion of the separator, the sensor having a pressing member which presses the separator toward the rear end, wherein the method comprises: a butting step of, in a state where the sensor terminal members are positioned inside the separator, the pressing member is held by an outer periphery of the tip end side portion of the separator, and the flange portion of the separator and the step portion or the inner projection of the metal outer tube butt against each other, moving at least one of the metal outer tube and the metal shell in a direction along which the metal outer tube and the metal shell approach each other, thereby causing the tip end portion of the metal outer tube to butt against the metal shell; and a deforming step of, in a state where the sensor terminal members are positioned inside, the flange portion of the separator in which the pressing member is held by the outer periphery of the tip end side portion, and the step portion or the inner projection of the metal outer tube butt against each other, and the pressing member butts against the tip end side face of the flange portion of the separator, radially inward pressing a portion of the metal outer tube to form a deformed portion which inward protrudes, the portion being positioned in a radially outer side of the pressing member, and deform also the pressing member so that the pressing member presses the separator toward the rear end.

In the conventional art described above, in the state where the lead wire 1081 and the like are not passed through the insulating member 1005, the insulating member 1005 is attached and fixed to the inside of the first metal cover 1003 by using the elastic member 1006. Therefore, the lead wire 1081 and the like must be then passed through the insulating member 1005 in the state where it is held inside the first metal cover 1003, and the lead terminal 1071, the connector 1075, and the like must be placed inside the insulating member 1005. Consequently, the work is cumbersome, and, when the positions of the lead terminal 1071, the connector 1075, and the like are deviated, stresses are easily applied to the lead terminal and the like during a process of attaching the separator.

It may be contemplated that, conversely, the lead wire 1081 is passed through the insulating member 1005, the lead terminal 1071, the connector 1075, and the like are placed inside insulating member 1005, and the insulating member 1005 in this state is then attached to the inside of the first metal cover 1003. In this case, however, the connector 1075, the lead wire 1081, and the like exist inside the insulating member 1005, and hence it is difficult to pressingly insert the elastic member 1006 between the insulating member 1005 and the first metal cover 1003.

By contrast, in the method of producing a sensor of the invention, a separator in which the sensor terminal members are positioned inside the separator, and the pressing member is attached and held to the tip end side portion is previously prepared. Thereafter, one of the butting step and the deforming step is first conducted, and the other step is then conducted.

In the butting step, in the state where the flange portion of the separator and the step portion or the inner projection of the metal outer tube butt against each other, at least one of the metal outer tube and the metal shell is moved in a direction along which they approach each other, thereby causing the tip end portion of the metal outer tube to butt against the metal shell. By contrast, in the deforming step, in the state where the flange portion of the separator and the step portion or the inner projection of the metal outer tube butt against each other, the deformed portion is formed, and also the pressing member is deformed, so that the separator is pressed toward the rear end by the pressing member to cause the flange portion of the separator and the step portion or the inner projection of the metal outer tube to be in close contact with each other.

According to the configuration, in the work of placing the sensor terminal members inside the separator, the metal outer tube does not impede the work, and hence the work can be easily conducted. Unlike the conventional art described above, moreover, it is not required to pressingly insert the elastic member into the metal outer tube before the tip end portion of the metal outer tube is caused to butt against the metal shell. Namely, the fixation of the separator can be conducted either before or after the metal outer tube is caused to butt against the metal shell. Moreover, when the deformed portion is formed from the outside of the metal outer tube, the separator can be pressed toward the rear end. Therefore, the fixation can be easily conducted without being affected by the sensor terminal members placed in the separator, and the like.

Since the tip end portion of the metal outer tube is caused to butt against the metal shell, the longitudinal positions of the metal outer tube and the separator with respect to the metal shell can be determined.

The tip end portion of the metal outer tube and the metal shell which butt against each other can be connected to each other by a caulking process or laser welding. Alternatively, the tip end portion of the metal outer tube and the metal shell may be provisionally fixed to each other by a caulking process, and, after the deforming step and the like are conducted, they may be connected to each other by laser welding. Alternatively, while the tip end portion of the metal outer tube is kept to be pressed against the metal shell, production steps may proceed without conducting provisional fixation and welding, and, after the pressing member is deformed in the deforming step, the tip end portion of the metal outer tube and the metal shell may be connected to each other by laser welding or the like.

Preferably, the method of producing a sensor is a method of producing a sensor in which the rear end side face of the flange portion of the separator forms an inclined face which is more radially outward positioned as further advancing toward the tip end, and the step portion or the inner projection of the metal outer tube has a flange butting face forming an inclined face which butts against the rear end side face of the separator, and which is more radially outward positioned as further advancing toward the tip end.

In the method of producing a sensor of the invention, the rear end side face of the flange portion of the separator butts against the flange butting face of the step portion or the inner projection of the metal outer tube, and both the rear end side face of the flange portion (the rear end side face corresponds to the outer-tube butting face) and the flange butting face of the metal outer tube form an inclined face which is more radially outward positioned as further advancing toward the tip end. In the deforming step, when the separator is pressed toward the rear end by the pressing member, therefore, the separator moves along the inclined face in a direction along which the axis of the separator coincides with that of the metal outer tube, and hence the position of the separator with respect to the metal outer tube can be adequately determined. Since the position of the separator with respect to the metal outer tube can be adequately determined, also the position of the sensor terminal members held by the separator can be correctly determined. As a result, in the sensor, a defect such as destruction of the sensor element or breakage of the sensor terminal members due to application of stress on the sensor terminal members themselves or between the sensor terminal members and the sensor element because of positional or postural deviation of the sensor terminal members can be prevented from occurring, the separator can be stably fixed to the inside of the metal outer tube, and the reliability is high.

Preferably, any one of the methods of producing a sensor is a method of producing a sensor in which the pressing member has: a metal tube portion having an inner diameter which is larger than an outer diameter of the tip end side portion of the separator, and an outer diameter which is smaller than an inner diameter of the metal outer tube; and an elastic holding portion which, when the metal tube portion is attached to the tip end side portion of the separator, elastically butts against the tip end side portion of the separator inside the metal tube portion, to hold the metal tube portion to the separator, and, in accordance with the formation of the deformed portion of the metal outer tube in the deforming step, the tip end side face of the flange portion of the separator is pressed toward the rear end by the rear end of the metal tube portion.

In the method of producing a sensor of the invention, the pressing member of a simple structure having the metal tube portion and the elastic holding portion is used. The pressing member can be easily attached to the tip end side portion of the separator, and can be economically produced. When the deformed portion is formed in the metal outer tube, moreover, a portion of the metal tube portion which is on the side of the rear end with respect to a portion that is deformed in accordance with the formation moves slightly toward the rear end. Therefore, the rear end of the metal tube portion presses and presses the tip end side face of the flange portion of the separator toward the rear end. In other words, in the tip end side face of the flange portion of the separator, the butting portion with respect to the pressing member exists in an annular form, and they are in point contact with each other as seen in a radial direction. As compared with the case where, although the separator is similarly pressed toward the rear end, the butting portion has a width and annularly extends, therefore, the posture of the separator (for example, deviation of the axis of the separator with respect to that of the metal outer tube, inclination of the axis, and rotation) can be changed in a relatively easy manner during a process of assembling the sensor. Consequently, the posture of the separator is changed during a process of assembling the sensor, so that stresses are hardly applied to the sensor terminal members, the lead wires, and the like. As a result, the resulting sensor is a sensor in which a defect such as breakage of the sensor terminal members or the lead wires can be prevented from occurring, and which is highly reliable.

Preferably, the method of producing a sensor is a method of producing a sensor in which the elastic holding portion of the pressing member is formed in three or more places which are arranged at regular intervals in a circumferential direction of the metal tube portion.

Since the elastic holding portion of the pressing member is formed in three or more places which are arranged at regular intervals in a circumferential direction, the tip end side face of the flange portion of the separator can be adequately pressed toward the rear end.

Preferably, the method of producing a sensor is a method of producing a sensor in which the metal tube portion of the pressing member has a rear end portion which is curved inward or outward in a radial direction.

The rear end of the metal tube portion butts against the tip end side face of the flange portion of the separator. When the posture of the separator is to be changed, therefore, friction is produced between the tip end side face of the separator and the end face of the rear end of the metal tube portion, to try to impede the posture change of the separator. In the invention, the rear end portion of the metal tube portion has the inward or outward curved shape, and hence the tip end face of the separator butts against the curved rear end portion. Therefore, friction with respect to the tip end side face of the separator can be reduced, so that the posture change of the separator can be conducted more easily.

Preferably, any one of the methods of producing a sensor is a method of producing a sensor in which the elastic holding portion of the pressing member is a J-shaped elastic holding portion which is positioned in the rear end of the metal tube portion, which elongates radially inward, and which is gradually changed in direction to elongate toward the tip end to be curved into a substantially J-like shape.

In the method of producing a sensor of the invention, the pressing member in which the elastic holding portion is a J-shaped elastic holding portion having a substantially J-like shape is used. When the elastic holding portion is a J-shaped elastic holding portion, a more adequate elasticity can be easily obtained by adjusting the radius, width, or the like of the curved portion.

Preferably, any one of the methods of producing a sensor is a method of producing a sensor in which, in a state where the outer-tube butting face of the separator and the flange butting face of the metal outer tube butt against each other, the flange portion of the separator is smaller in diameter than a portion of the metal outer tube surrounding the flange portion, and a portion of the metal tube portion of the pressing member, the portion being positioned on the side of the rear end with respect to the deformed portion of the metal tube portion which is formed in the deforming step, is smaller in diameter than a portion of the metal outer tube surrounding the portion, and larger in diameter than the flange portion.

According to the methods of producing a sensor, even in the case where a stone or the like hits the peripheral portion of the flange portion of the metal outer tube or a portion between it and the deformed portion and the metal outer tube is largely depressed, a part of the metal tube portion which is large in diameter than the flange portion bumps against the metal outer tube before the depressed metal outer tube bumps against the flange portion, thereby absorbing the shock. Therefore, breakage such as that in which the depressed metal outer tube violently collides with the flange portion and the separator including the flange portion cracks can be prevented from occurring.

Preferably, the method of producing a sensor is a method of producing a sensor in which the pressing member is a cylindrical rubber member having an inner diameter which is smaller than an outer diameter of the tip end side portion of the separator, and an outer diameter which, when the member is attached to the tip end side portion of the separator, is smaller than an inner diameter of the metal outer tube, and, in accordance with the formation of the deformed portion of the metal outer tube in the deforming step, is deformed to press the tip end side face of the flange portion of the separator toward the rear end.

In the method of producing a sensor, since a cylindrical rubber member is used as the pressing member, the handling is facilitated.

Preferably, any one of the methods of producing a sensor is a method of producing a sensor in which the sensor element is a cylindrical gas sensor element in which a tip end side is closed, the sensor has: a rod heater which is inserted into a bottomed hole of the gas sensor element; and one or more heater terminal members which are electrically connected to the heater, the separator holds insulation between the sensor terminal members and the heater terminal members, the butting step is conducted in a manner that, in a state where the separator is loosely inserted into the metal outer tube, at least one of the metal outer tube and the metal shell is moved in a direction along which they approach each other, to cause the tip end portion of the metal outer tube to butt against the metal shell, and the heater is inserted into the gas sensor element held by the metal shell, and the deforming step is conducted after the butting step.

In the method of producing a sensor of the invention, a cylindrical gas sensor element in which a tip end side is closed is used as the sensor element, the sensor element comprises a heater, and, in the butting step, the tip end portion of the metal outer tube is caused to butt against the metal shell, and moreover the heater is inserted into the gas sensor element.

If the deforming step is conducted in advance of the butting step, the separator is fixed to the metal outer tube. In the case where the heater is inserted into the bottomed hole of the gas sensor element with being largely inclined because of deviation of the placement of heater connecting terminals in the separator or the like, therefore, stresses are applied to the heater, and a defect such as that the heater is bent, or that portions connecting the heater with the heater connecting terminals are broken may occur.

By contrast, in the production method of the invention, the heater is inserted into the gas sensor element in the butting step, and the deforming step is then conducted. In the butting step, the separator is loosely inserted into the metal outer tube. When stresses are applied to the heater, the heater terminal members, and the like in accordance with the insertion of the heater, therefore, the position of the separator, the inclination of the axis, and the like are adjusted so as to reduce the stresses. Thereafter, the separator is fixed to the metal outer tube with being pressed by the pressing member in the deforming step. Consequently, the resulting sensor is a sensor (gas sensor) in which smaller stresses are applied to the heater and the heater terminal members, and a defect such as that the heater is bent or broken hardly occurs, and which is highly reliable. An example of the heater is a rod heater having a circular section shape or a rectangular section shape.

Preferably, the method of producing a sensor is a method of producing a sensor in which the butting step includes an inserting and positioning step of positioning and inserting a tip end of the heater to be guided into a rear end opening of the gas sensor element, the tip end further protruding toward the tip end than the tip end portion of the metal outer tube.

In the method of producing a sensor of the invention, the butting step includes the inserting and positioning step, and the tip end of the heater is guided into the rear end opening of the gas sensor element. Therefore, the heater can be easily inserted, and it is possible to eliminate a defect such as that the tip end of the heater butts against a rear end portion of the gas sensor element and the heater is bent.

Preferably, the method of producing a sensor is a method of producing a sensor in which the inserting and positioning step is conducted by gripping a part of a portion of the heater which further protrudes toward the tip end than the tip end portion of the metal outer tube, by a chuck device, and adjusting a position of the tip end of the heater.

In the method of producing a sensor, in the inserting and positioning step, the tip end of the heater is guided by the chuck device, and hence the tip end of the heater can be inserted easily and surely into the rear end opening of the gas sensor element.

The further solving means is an assembly of a separator and a pressing member which is to be used in a sensor, the sensor having: a sensor element; a metal shell which holds the sensor element; one or more sensor terminal members which are electrically connected to the sensor element, and which elongate from the sensor element toward a rear end; a metal outer tube which is connected to the metal shell at a tip end portion of the metal outer tube itself; and an electrically insulative separator which is housed inside the metal outer tube, the separator including: a rear end side portion which is positioned on a side of the rear end; a tip end side portion which is positioned on a side of a tip end;

and a flange portion which is positioned at a middle between the rear end side portion and the tip end side portion, which is larger in diameter than the rear end side portion and the tip end side portion, and which has a tip end side face facing the tip end side between the flange portion and the tip end side portion, and an outer-tube butting face facing the rear end side between the flange portion and the rear end side portion, the sensor terminal members being positioned inside, the separator providing at least one of insulation between the sensor terminal members, and insulation between the sensor terminal members and the metal outer tube, the metal outer tube having a step portion or an inner projection which has a flange butting face butting against the outer-tube butting face of the flange portion of the separator, the sensor having a pressing member which presses the separator toward the rear end, wherein the pressing member has: a metal tube portion having an inner diameter which is larger than an outer diameter of the tip end side portion of the separator, and an outer diameter which is smaller than an inner diameter of the metal outer tube; and an elastic holding portion which is placed inside the metal tube portion, the elastic holding portion elastically butts against the tip end side portion of the separator, and the pressing member is held by the separator.

In the assembly of the invention, the pressing member is held by the separator by means of the elastic force of itself. When the assembly is used in production of a sensor, therefore, less labor is required, and the sensor can be more economically produced as compared with the case where the separator and the pressing member are separately attached.

BRIEF DESCRIPTION OF THE DRAWINGS

FIG. 12 is a partial enlarged view showing a manner of deforming the metal outer tube and the pressing metal part in the deforming step, (a) shows a state before deformation, and (b) shows a state after deformation.

Figure 1:
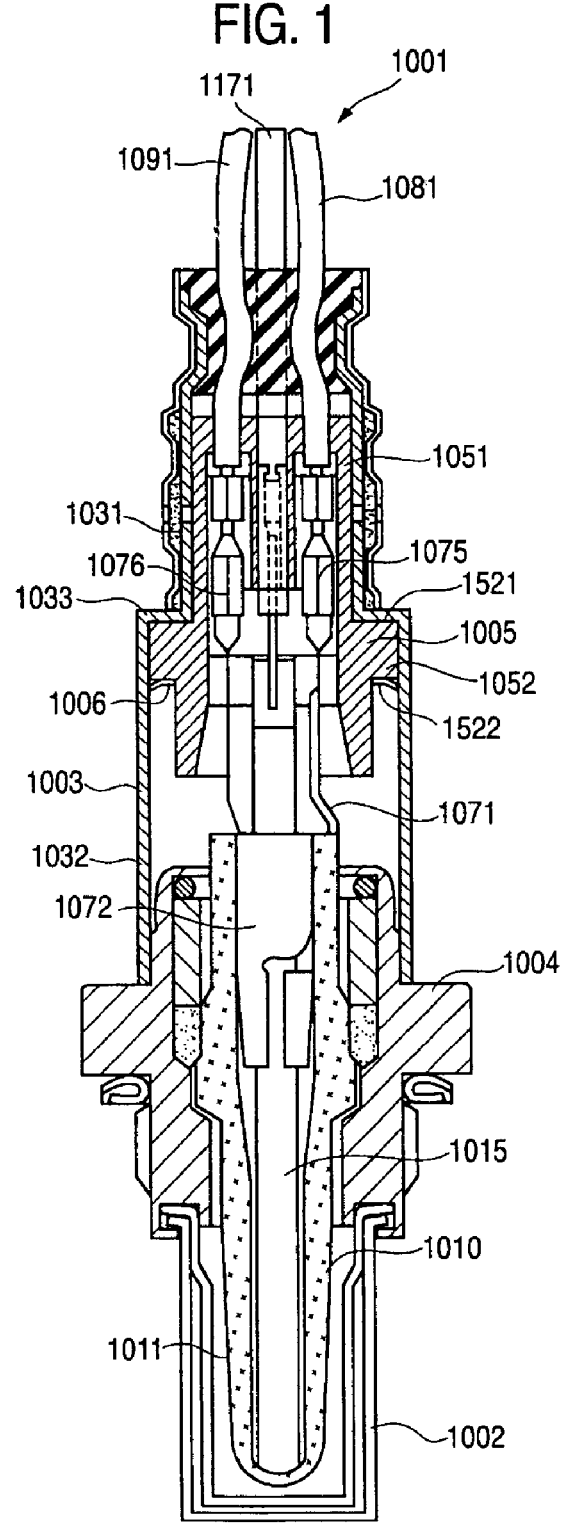
FIG. 1 is an explanatory view showing the whole configuration of a gas sensor of the conventional art.

The reference numerals in the figures are as follows:
1 oxygen sensor (gas sensor, sensor)
2 oxygen sensor element (gas sensor element, sensor element)
2a bottomed hole
2b sensor external electrode layer
2c sensor internal electrode layer
2h rear end opening
3 metal shell
3d connecting portion
11 first sensor terminal metal part (sensor terminal member)
12 second sensor terminal metal part (sensor terminal member)
13, 14 sensor output lead wire
15 heater
15d rear end face
16, 17 heater terminal metal part (heater terminal member)
18, 19 heater lead wire
21 metal outer tube
22a tip end portion
24 inner projection
24b flange butting face
31 separator
33 tip end side portion
34 flange portion
34a outer-tube butting face
34b tip end side face
39 assembly (assembly of separator and pressing member)
41 pressing metal part (pressing member)
42 metal tube portion
42b rear end portion (of metal tube portion)
43 J-shaped elastic holding portion
43a butting portion
CH chuck mechanism

BEST MODE FOR CARRYING OUT THE INVENTION

Figure 2:
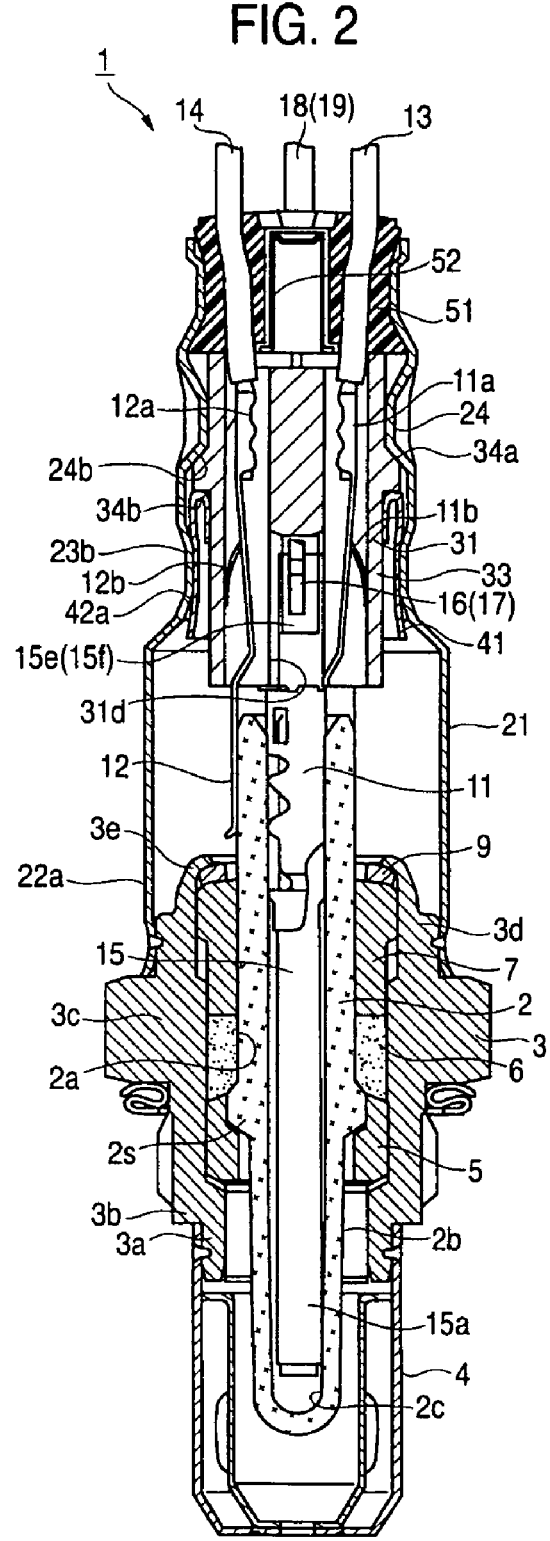
FIG. 2 is an explanatory view showing the whole configuration of a gas sensor of an embodiment.

An embodiment of the invention will be described with reference to FIGS. 2 to 14. FIG. 2 is an explanatory view showing the whole configuration of an oxygen sensor 1 of the embodiment. The oxygen sensor 1 comprises a hollow shaft-like oxygen sensor element 2 in which the tip end is closed, and a heater 15 which is inserted into a bottomed hole 2a of the oxygen sensor element 2. The oxygen sensor element 2 is formed into a hollow shaft-like shape by a solid electrolyte having an oxygen ion conductivity.

A typical example of such a solid electrolyte is ZrO2 into which Y2O3 or CaO is solid-dissolved. A solid solution of an oxide of another alkaline earth metal or rear earth metal and ZrO2 may be used. Furthermore, ZrO2 serving as a basic component may contain HfO2.

On the inner face of the bottomed hole 2a of the oxygen sensor element 2, a sensor internal electrode layer 2c which is formed as a porous member by, for example, Pt or a Pt alloy is formed so as to cover a substantially whole of the inner face. On the other hand, a sensor external electrode layer 2b of a similar porous member is disposed on a tip end portion of the outer face of the oxygen sensor element 2 (see FIG. 4). An engagement flange portion 2s which radially outward protrudes is disposed in an axially middle portion of the oxygen sensor element 2. The engagement flange portion 2s is engaged and held by insulators 5, 7 made of insulative ceramic, and ceramic powder 6 formed by talc, whereby the oxygen sensor element 2 is airtightly held by a cylindrical metal shell 3 which has a passage hole at the center. The oxygen sensor element 2 is passed through the passage hole. In this description, among the directions along the axis of the oxygen sensor element 2 (the vertical directions in FIG. 2), the side directed toward the tip end portion (the closed side, the lower portion in FIG. 2) is referred to as "tip end side", and the side directed in the opposite direction (the upper portion in FIG. 2) is referred to as "rear end side".

The metal shell 3 has a threaded portion 3b and a hexagonal portion 3c which are used for attaching the oxygen sensor 1 to an attachment portion of an exhaust pipe or the like. A protector 4 is connected to a protector connecting portion 3a by laser welding. The protector 4 is attached so as to cover a tip end portion of the oxygen sensor element 2 which protrudes from a tip end opening of the metal shell 3. The oxygen sensor 1 is used while a portion which is on the side of the tip end with respect to the threaded portion 3b is positioned in an engine such as an exhaust pipe, and a portion which is on the side of the rear end is positioned in the outside or the atmosphere. A plurality of gas passage ports through which exhaust gas can be passed are formed in the protector 4.

By contrast, a rear end portion 3e of the metal shell 3 is airtightly held with being caulked with the insulator 7 via a ring packing 9. A tip end portion 22a of a cylindrical metal outer tube 21 is secured to a connecting portion 3d on the rear end side of the hexagonal portion 3c by laser welding from the outside. A grommet 51 made of rubber and the like is fitted into a rear end opening of the metal outer tube 21, and then subjected to caulking to attain sealing. A filter member 52 which introduces the atmosphere into the metal outer tube 21, and which prevents water from entering is placed in a center portion of the grommet 51. A separator 31 made of insulative alumina ceramic is disposed on the tip end side of the grommet 51. Sensor output lead wires 13, 14 and heater lead wires 18, 19 are placed so as to pass through the separator 31 and the grommet 51 (see FIGS. 2 and 4).

Figure 3:
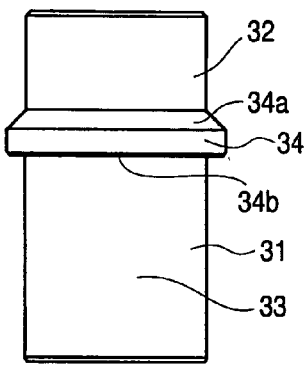
FIG. 3(a) is a side view of a separator, (b) is a plan view, (c) is a bottom view, (d) is a section view taken along A—A, and (e) is a section view taken along B—B.
Figure 3:
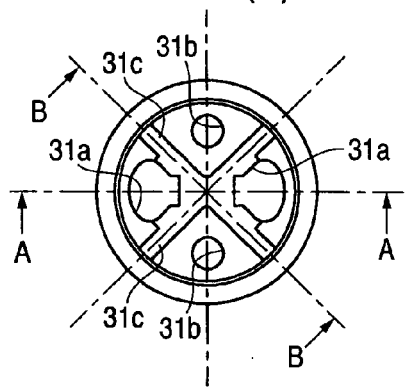
Figure 3:
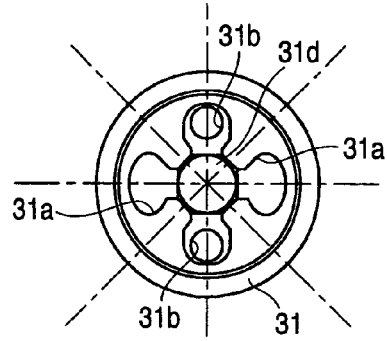
Figure 3:
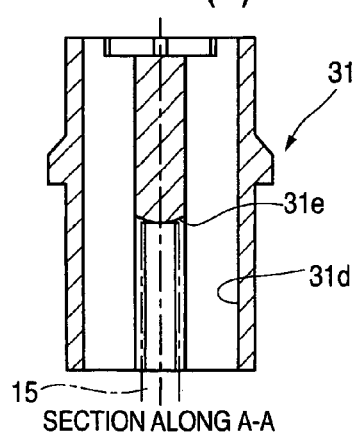
Figure 3:
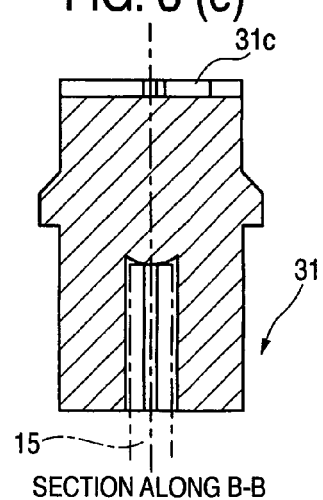

As shown in a side view (see FIG. 3(*a*)), the separator 31 shown in FIG. 3 has a rear end side portion 32, a tip end side portion 33, and a flange portion 34 which is positioned between them, and which is larger in diameter than them. In the flange portion 34, an outer-tube butting face 34a in which the diameter is made larger as further advancing toward the tip end side (the lower portion in FIG. 2) to form a tapered face is formed between the flange portion and the rear end side portion 32. By contrast, a tip end side face 34b which forms a stepwise level difference is formed between the flange portion and the tip end side portion 33. As shown in FIGS. 3(*b*), (*c*), lead wire passage holes 31a, 31b through which the lead wires 13, 14, 18, 19 are to be passed are formed so as to axially pass through the separator 31. In an end face on the rear end side, an air vent channel 31c is formed at a position where the channel does not interfere with the four lead wire passage holes 31a, 31b, in a cross pattern and in a direction perpendicular to the axis. A bottomed holding hole 31d which is opened in the tip end face of the separator 31 is formed in the axial direction.

Figure 4:
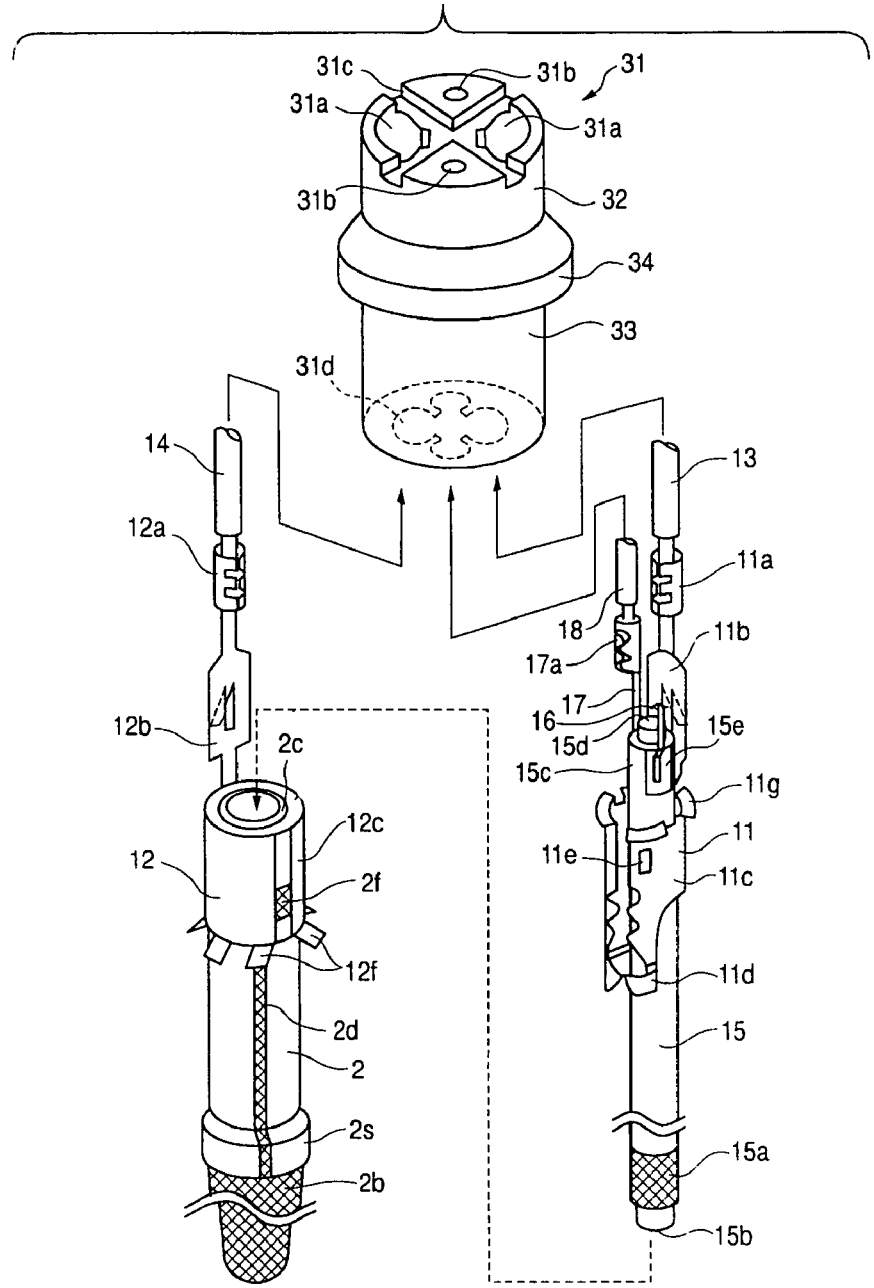
FIG. 4 is an exploded perspective view showing a state of attaching an oxygen sensor element and a heater to the separator.
Figure 5:
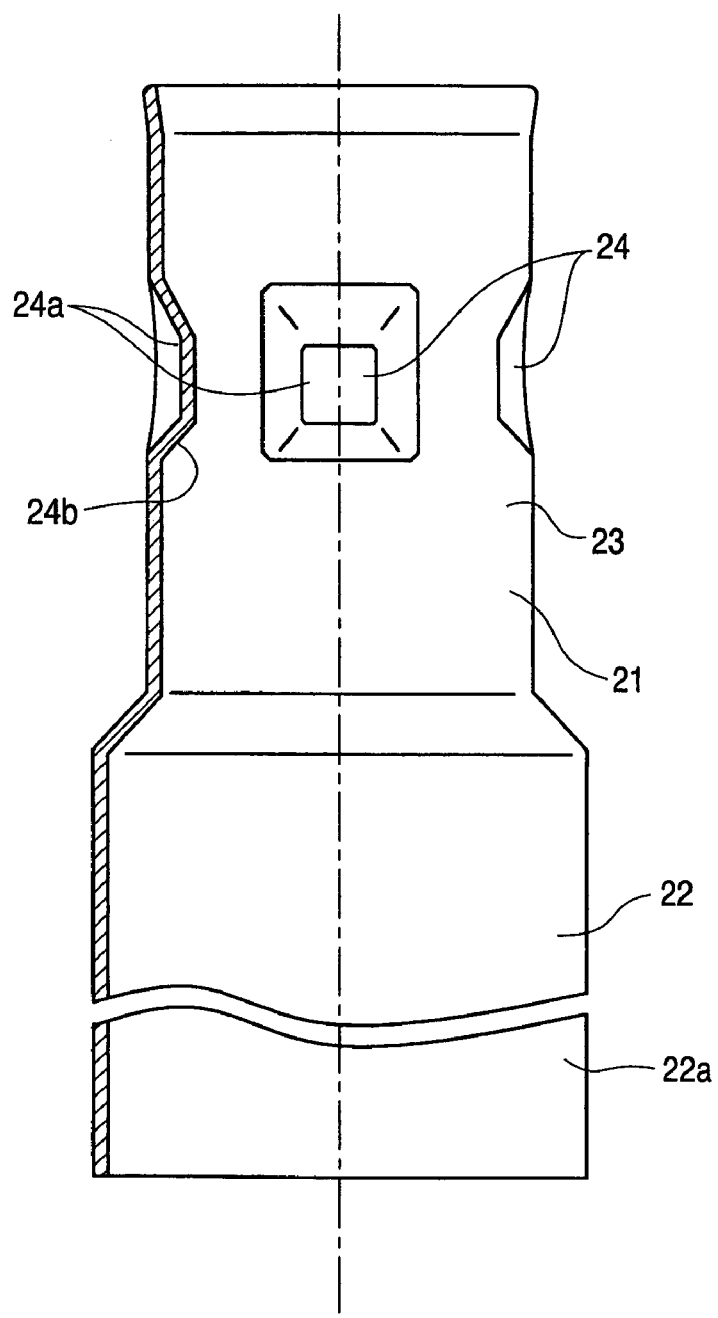
FIG. 5 is a partially cutaway side view of a metal outer tube.

As shown in FIGS. 2 and 4, the lead wires 13, 14, 18, 19 are passed through the holding hole 31d and the lead wire insertion holes 31a, 31b, and connector portions 11a, 12a of first and second sensor terminal metal parts 11, 12, and heater terminal metal parts 16, 17 are held inside the separator 31 while being insulated from one another.

As shown in FIG. 3(*d*), the bottom face 31e of the holding hole 31d is positioned in an axially middle portion of the separator 31. A rear end portion 15c of the heater 15 is inserted into the holding hole 31d from the axial tip end side of the separator 31, and the rear end face 15d of the heater 15 butts against the bottom face 31e of the holding hole 31d, whereby the heater 15 is positioned in the axial direction with respect to the separator 31.

As shown in FIG. 4, the first sensor terminal metal part 11 has the connector portion 11a, a separator butting portion 11b, and an insertion portion 11c which are integrally molded. Among the components, the connector portion 11a grips a core wire of the sensor output lead wire 13 to electrically connect the first sensor terminal metal part 11 and the sensor output lead wire 13. The separator butting portion 11b elastically butts against the holding hole 31d of the separator 31 (see FIG. 2) to hold the first sensor terminal metal part 11 in the separator 31. The insertion portion 11c is inserted into the bottomed hole 2a of the oxygen sensor element 2 to be electrically connected to the sensor internal electrode layer 2c. The insertion portion 11c includes a lower pressing portion 11d and an upper pressing portion 11e. When the insertion portion 11c is inserted into the bottomed hole 2a of the oxygen sensor element 2, the insertion portion 11c presses the heater 15 surrounded thereby, to cause the axis of the heater 15 to deviate from the center axis of the oxygen sensor element 2, whereby the posture of the heater 15 is adjusted so that a heating portion 15a is in contact with the inner wall (the sensor internal electrode layer 2c) of the bottomed hole 2a of the oxygen sensor element 2. A flange portion 11g is disposed in the rear end side of the insertion portion 11c in order to prevent the insertion portion 11c from entering the bottomed hole 2a of the oxygen sensor element 2.

When the heating portion 15a formed in the heater is made eccentric to be in contact with the inner wall of the bottomed hole 2a of the oxygen sensor element 2, the thermal energy is concentrated into a smaller volume. This is effective in shortening the activation time of the oxygen sensor 1.

On the other hand, the second sensor terminal metal part 12 has the connector portion 12a, a separator butting portion 12b, and a gripping portion 12c which are integrally molded. Among the components, the connector portion 12a grips a core wire of the sensor output lead wire 14 to electrically connect the second sensor terminal metal part 12 and the sensor output lead wire 14. The separator butting portion 12b elastically butts against the holding hole 31d of the separator 31 (see FIG. 2) to hold the second sensor terminal metal part 12 in the separator 31. The gripping portion 12c grips the outer periphery of the vicinity of rear end of the oxygen sensor element 2.

As shown in FIG. 4, the oxygen sensor element 2 has a connecting layer 2f which is formed in a rear end portion, and which is electrically connected to the sensor external electrode layer 2b via a leading layer 2d. The gripping portion 12c is electrically connected to the connecting layer 2f to be electrically connected also to the sensor external electrode layer 2b. A flange portion 12f is disposed in the tip end side of the gripping portion 12c in order to allow the rear end portion of the oxygen sensor element 2 to be easily inserted into the gripping portion 12c. The leading layer 2d and the connecting layer 2f are formed by baking.

As shown in FIGS. 2 and 4, the heater 15 is a rod ceramic heater, and the heating portion 15a having a resistance heating element (not shown) is formed on a core member which is mainly made of alumina. When the heater 15 is energized through the heater terminal metal parts 16, 17 which are brazed to electrode pads 15e, 15f, and the heater lead wires 18, 19, the tip end portion of the oxygen sensor element 2 is heated. The heater terminal metal part 17 has a connector portion 17a which grips a core wire of the heater lead wire 18 to electrically connect the heater terminal metal part 17 and the heater lead wire 18. Although not shown in FIG. 4, the heater terminal metal part 16 similarly has a connector portion which grips a core wire of the heater lead wire 19.

The metal outer tube 21 (see FIG. 5) has: a first outer tube potion 22 which is made of a metal, which is formed into a substantially cylindrical shape, which is positioned on the side of the tip end (the lower side in the figure), and in which the tip end portion 22a on the tip end side is joined to the metal shell 3 as described above; and a second outer tube potion 23 which is positioned on the rear end side with respect to the first outer tube potion, and which is smaller in diameter than the first outer tube potion. In an axially middle portion of the second outer tube potion 23, an inner projection (first reduced-diameter portion) 24 in which a projection top face 24a protrudes in a rectangular shape toward the radially inner side is formed in four places equally arranged in a circumferential direction. In each of the inner projections 24, a flange butting face 24b forming an inclined face is formed on the tip end side with respect to the projection top face 24a. As shown in FIG. 2, the flange butting face 24b butts against the outer-tube butting face 34a of the separator 31.

Figure 6:
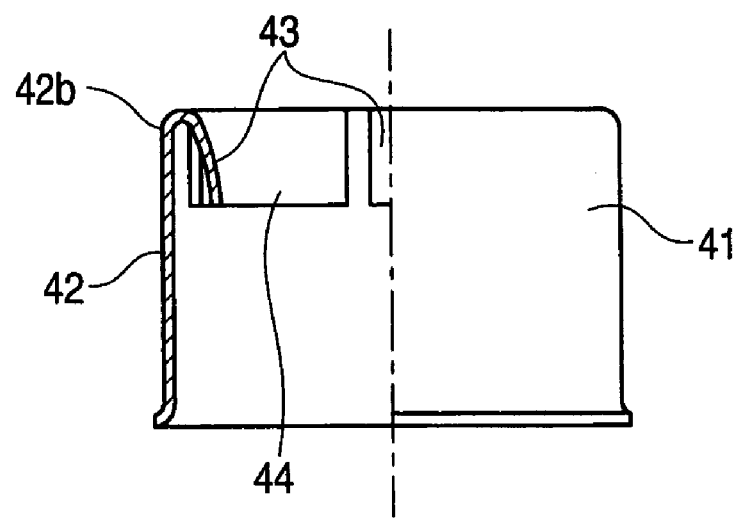
FIG. 6 is a partially cutaway side view of a pressing metal part.

As shown in FIG. 2, a pressing metal part 41 is attached to the periphery of the tip end side portion 33 of the separator 31. As shown in FIG. 6, the pressing metal part 41 has a cylindrical metal tube portion 42, and also J-shaped elastic holding portions 43 and tube elongating portions 44 which are formed in a rear end portion 42a of the metal tube portion 42 and integrally with the metal tube portion 42. The J-shaped elastic holding portions 43 are scattered in four places arranged at regular intervals in a circumferential direction, and elongate toward the radially inner side, and their direction is gradually changed so that the portions elongate toward the tip end side to be curved into a substantially J-like shape. When the pressing metal part 41 is attached to the tip end side portion 33 of the separator 31, the J-shaped elastic holding portions 43 are elastically deformed to hold the pressing metal part 41 to the tip end side portion 33 (see FIG. 7). The holding strength can be adjusted by the width and shape of the J-shaped elastic holding portions 43, and the like. The tube elongating portions 44 are formed between the J-shaped elastic holding portions 43, and inward curved into a J-like shape in the same manner as the J-shaped elastic holding portions 43. However, their curvatures are adjusted so that the J-shaped elastic holding portions 43 protrude further radially inward than the tube elongating portions 44. In accordance with formation of a deformed portion (second reduced-diameter portion) in the second outer tube potion 23 of the metal outer tube 21, a deformed portion 42a is formed also in the metal tube portion 42 as described later, so that the metal tube portion 42 presses the tip end side face 34b of the separator 31, and hence the separator 31 toward the rear end. Since the curved tube elongating portions 44 and the J-shaped elastic holding portions 43 are disposed in the rear end portion 42a of the metal tube portion 42 in this way, the posture of the separator 31 is hardly prevented from being changed when the metal tube portion butts against the tip end side face 34b of the separator 31 during a process of producing the oxygen sensor 1 as described later.

Figure 7:
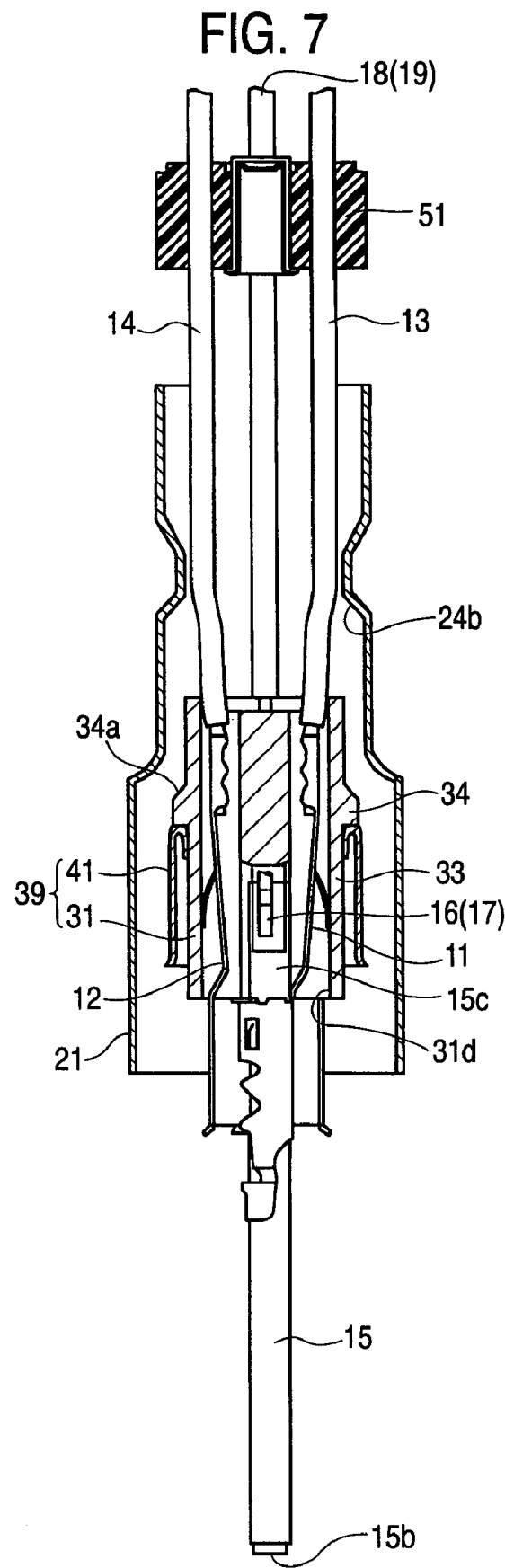
FIG. 7 is an explanatory view showing a state where a separator in which sensor terminal metal parts and the like are held is placed in the metal outer tube.

The oxygen sensor 1 is produced in the following manner. The sensor output lead wires 13, 14 are previously connected to the connector portions 11a, 12a of the first and second sensor terminal metal parts 11, 12, respectively. The heater lead wires 18, 19 are previously connected to the connector portion 17a and the like of the heater terminal metal parts 16, 17. As shown in the right lower portion of FIG. 4, in the state where the heater 15 is positioned inside the insertion portion 11c of the first sensor terminal metal part 11, the lead wires 13, 14, 18, 19 are passed through the holding hole 31d and the lead wire passage holes 31a, 31b of the separator 31. As shown in FIG. 7, a part of the first and second sensor terminal metal parts 11, 12, the whole of the heater terminal metal parts 16, 17, and the rear end portion 15c of the heater 15 are then set to a state where they are held inside the holding hole 31d with being insulated from one another. As shown in FIG. 9(b), the pressing metal part 41 is attached to the outer periphery of the tip end side portion 33 of the separator 31 to constitute an assembly 39 (see FIG. 7) in such a manner that a butting portion 43a of the J-shaped elastic holding portion 43 (a rear end portion 42b of the metal tube portion 42) butts against the tip end side face 34b of the flange portion 34. In the embodiment, the separator 31 and the pressing metal part 41 are previously set as the assembly 39 so as to be integrally handled, and hence the separator 31 and the pressing metal part 41 can be easily handled in steps which are described below.

The left lower portion of FIG. 4 shows a state where the oxygen sensor element 2 and the second sensor terminal metal part 12 are connected to each other. However, the oxygen sensor element 2 and the second sensor terminal metal part 12 are connected to each other in the manner described later, and, in this stage, the second sensor terminal metal part 12 is not connected to the oxygen sensor element 2.

In this way, the separator 31 in which the lead wire 13 and the like are passed through, and which holds the first sensor terminal metal part 11 and the like is loosely inserted into the metal outer tube 21, and the lead wire 13 and the like are passed through the grommet 51.

Figure 8:
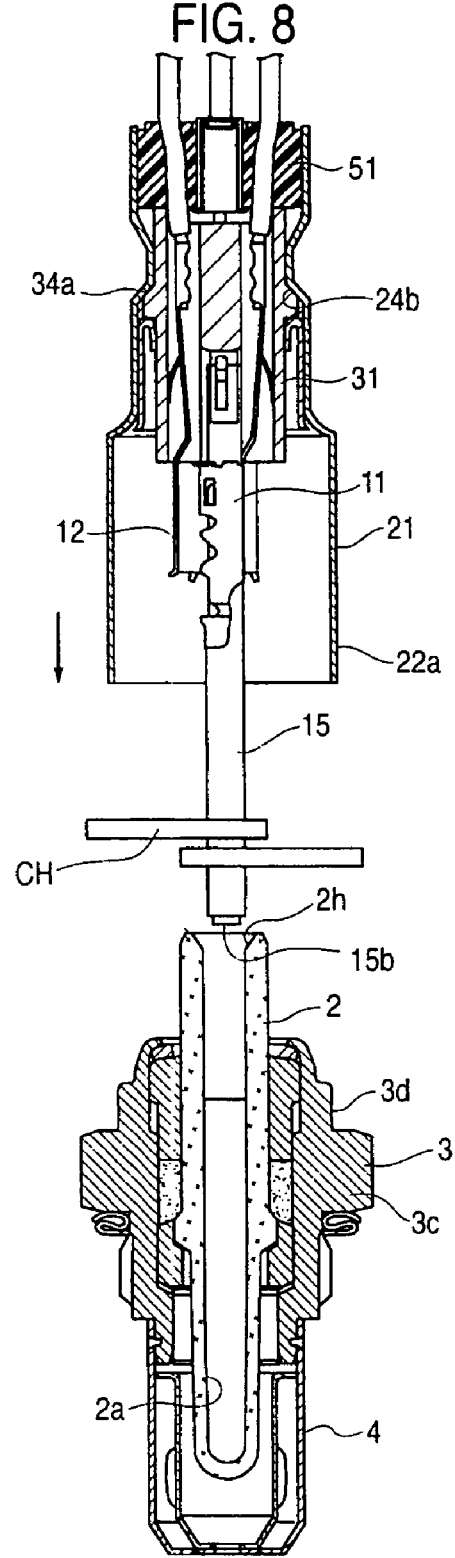
FIG. 8 is an explanatory view showing a manner of guiding and inserting the heater into a rear end opening of an oxygen sensor element.
Figure 9:
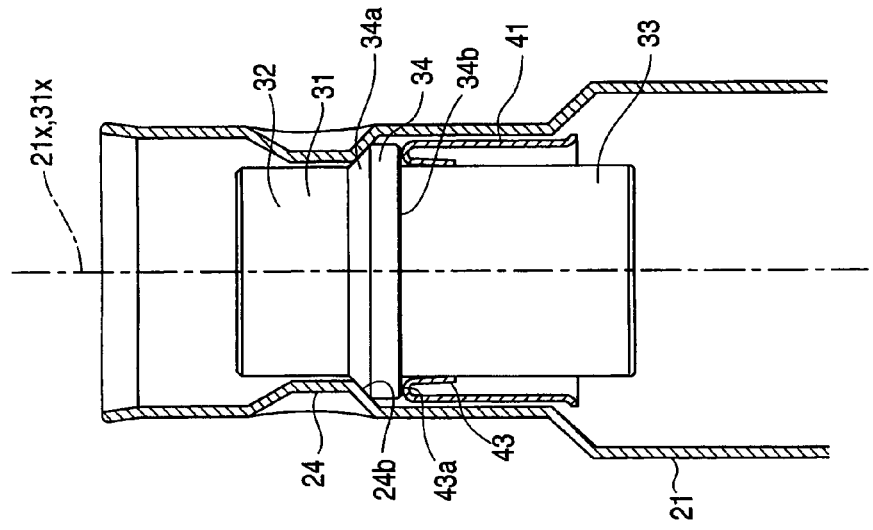
FIG. 9 is an explanatory view comparatively showing a case where an outer-tube butting face of a flange portion of the separator and a flange butting face of an inner projection of the metal outer tube are not tapered (a), and a case where they are tapered (b).
Figure 9:
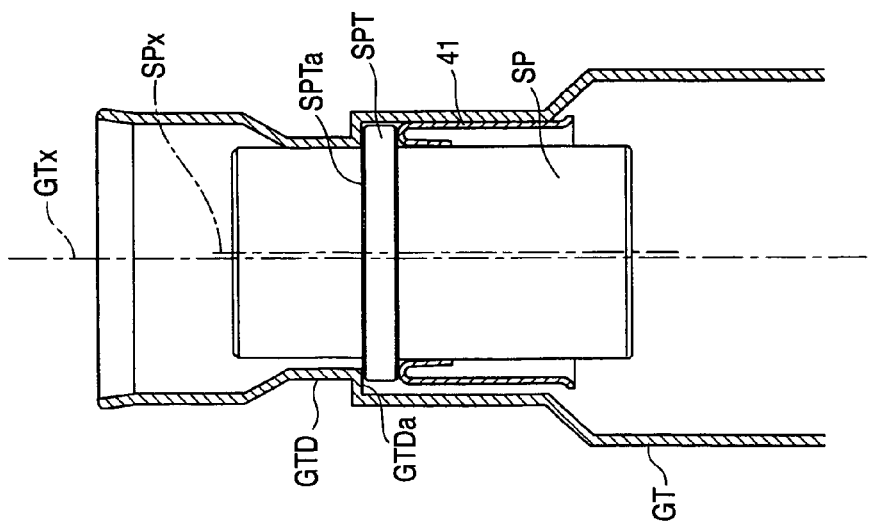

As shown in FIG. 8, previously, the oxygen sensor element 2 is secured to the metal shell 3, and the protector 4 is welded to the metal shell 3.

The positions of the oxygen sensor element 2 and the metal outer tube 21 are adjusted so that their axes coincide with each other, and a butting step is conducted as follows. The metal outer tube 21 is moved toward the tip end (the lower portion in the figure) to attain a state where the outer-tube butting face 34a of the separator 31 and the flange butting face 24b of the metal outer tube 21 butt against each other and the separator 31 is loosely inserted into the metal outer tube 21. The grommet 51 is fitted into the rear end portion of the metal outer tube 21. Furthermore, the metal outer tube 21 is moved toward the tip end (the lower portion in the figure). The heater 15 is then inserted into the bottomed hole 2a of the oxygen sensor element 2, and the metal outer tube 21 is moved toward the tip end until the tip end portion 22a of the metal outer tube 21 butts against the hexagonal portion 3c of the metal shell 3. The oxygen sensor element 2 and the metal shell 3, the metal outer tube 21 and the heater 15, and the separator 31 are requested only to be moved so as to relatively approach one another. In contrast to the above, the oxygen sensor element 2 and the metal shell 3 may be moved toward the rear end (the upper portion in the figure).

As a result, also the insertion portion 11c of the first sensor terminal metal part 11 is inserted together with the heater 15 into the bottomed hole 2a of the oxygen sensor element 2, to be electrically connected to the sensor internal electrode layer 2c. As a result of the insertion of the insertion portion 11c into the bottomed hole 2a of the oxygen sensor element 2, the axis of the heater 15 is inclined and deviated with respect to that of the oxygen sensor element 2, or adjusted so that the heating portion 15a of the heater 15 is in contact with the inner wall of the bottomed hole 2a. Moreover, the gripping portion 12c of the second sensor terminal metal part 12 grips the rear end portion of the oxygen sensor element 2 to be electrically connected to the connecting layer 2f.

In the embodiment, particularly, the heater 15 is inserted into the bottomed hole 2a of the oxygen sensor element 2, by pushing the rear end face 15d of the heater 15 with the bottom face 31e of the holding hole 31d of the separator 31. The separator 31 is moved with being pushed by the metal outer tube 21. When the metal outer tube 21 is moved toward the tip end until the tip end portion 22a of the metal outer tube 21 butts against the hexagonal portion 3c of the metal shell 3, therefore, the depth of the insertion of the heater 15 into the bottomed hole 2a of the oxygen sensor element 2 can be uniquely determined by the dimensions of the metal outer tube 21, the separator 31, and the heater 15, and hence it is not required to adjust the insertion depth.

Since the outer-tube butting face 34a is disposed in the separator 31, and the flange butting face 24b is disposed in the metal outer tube 21, the following advantages are attained in the butting step. This will be described with reference to FIG. 9.

FIG. 9(a) is an explanatory view comparatively showing a case where, unlike the embodiment, a tapered face is not disposed in a flange portion SPT of a separator SP, a step-like rear end side face SPTa is formed, and a step-like tip end side face GTDa is disposed also in a step portion GTD of a metal outer tube GT. Although lead wires and a heater are held in the separator SP, they are not shown in the figure.

The outer diameter of the flange portion SPT of the separator SP is smaller than the inner diameter of the metal outer tube. Therefore, the separator SP is allowed to be placed so that the axis SPx is deviated from the axis GTx of the metal outer tube GT. Even when, in this state, the metal outer tube GT is moved toward the tip end (the lower portion in the figure) and the heater which is not shown is inserted into an oxygen sensor element, no force which causes their axes GTx and SPx to coincide with each other acts. On the contrary, the movement of the separator SP is blocked by friction between the rear end side face SPTa of the separator SP and the tip end side face GTDa of the metal outer tube GT. While the axis SPx of the separator SP is deviated from the axis GTx of the metal outer tube GT, and hence the axis SPx of the separator SP is deviated also from the axis of the oxygen sensor element, therefore, the heater is inserted into the bottomed hole of the oxygen sensor element. Consequently, when the heater and the first sensor terminal metal part are inserted into the bottomed hole of the oxygen sensor element and the second sensor terminal metal part grips the oxygen sensor element, an oxygen sensor is produced in the state where stresses are generated among the heater, the first and second sensor terminal metal parts, the heater terminal metal parts, and the separator by the positional deviation of the separator SP. In an extreme case, therefore, there is the possibility that the stresses may cause defects such as that the terminal metal parts are ruptured, that the oxygen sensor element is broken, that the heater is bent, and that brazed portions between the heater and the heater terminal metal parts are damaged.

By contrast, in the embodiment shown in FIG. 9(b), the outer-tube butting face 34a forming an inclined face is disposed in the separator 31, and the flange butting face 24b forming an inclined face is disposed in the metal outer tube 21. When the metal outer tube 21 is moved toward the tip end (the lower portion in the figure) and the heater 15 and the insertion portion 11c of the first sensor terminal metal part 11 are inserted into the bottomed hole 2a of the oxygen sensor element 2 or the oxygen sensor element 2 is inserted to the gripping portion 12c of the second sensor terminal metal part 12, the friction resistance produced between them causes the outer-tube butting face 34a of the separator 31 to be pressed against the flange butting face 24b of the metal outer tube 21. Then, the separator 31 is moved so that the axis 31x of the separator 31 coincides with the axis 21x of the metal outer tube 21. Therefore, a phenomenon such as described above in which stresses due to positional deviation of the separator are generated in the heater 15, the first and second sensor terminal metal parts 11, 12, and the heater terminal metal parts 16, 17 is eliminated or reduced. As a result, the terminal metal parts, the heater, and the oxygen sensor element can be prevented from being broken or damaged, and the resulting oxygen sensor 1 is highly reliable.

In the above-described conventional art, the insulating member 1005 is fixed to the first metal cover 1003 by the elastic member 1006 (see FIG. 1). Unlike this, in the butting step in which the heater 15 is inserted into the oxygen sensor element 2, the separator 31 is not fixed to the metal outer tube 21, but in a loosely inserted state. In the case where the heater 15 and the first sensor terminal metal part 11 are inserted into the bottomed hole 2a of the oxygen sensor element 2 and the oxygen sensor element 2 is gripped by the second sensor terminal metal part 12, even when friction resistances are applied to these members and then transmitted to the separator 31, therefore, the separator 31 can be adequately moved in the form of inclination or the like. Consequently, stresses are hardly generated between the heater 15 and the terminal metal parts 11, 12, 16, 17, and the separator 31. Because of this also, the heater and the terminal metal parts can be prevented from being damaged.

Preferably, the butting step may include an inserting and positioning step in which, in an initial stage of the butting step, a chuck mechanism CH grips a portion of the heater 15 protruding from the metal outer tube 21 as shown in FIG. 8, and the position of the tip end 15b is adjusted so that the tip end can be guided to be inserted into a rear end opening 2h of the oxygen sensor element 2.

According to the configuration, even when the position of the tip end 15b of the heater 15 is deviated from a predetermined one because of the dimensional tolerance or bending of the heater terminal metal parts 16, 17, the heater 15 can be surely inserted into the bottomed hole 2a. After the tip end 15b of the heater 15 can be inserted into the rear end opening 2h, the chuck mechanism CH is released.

Figure 10:
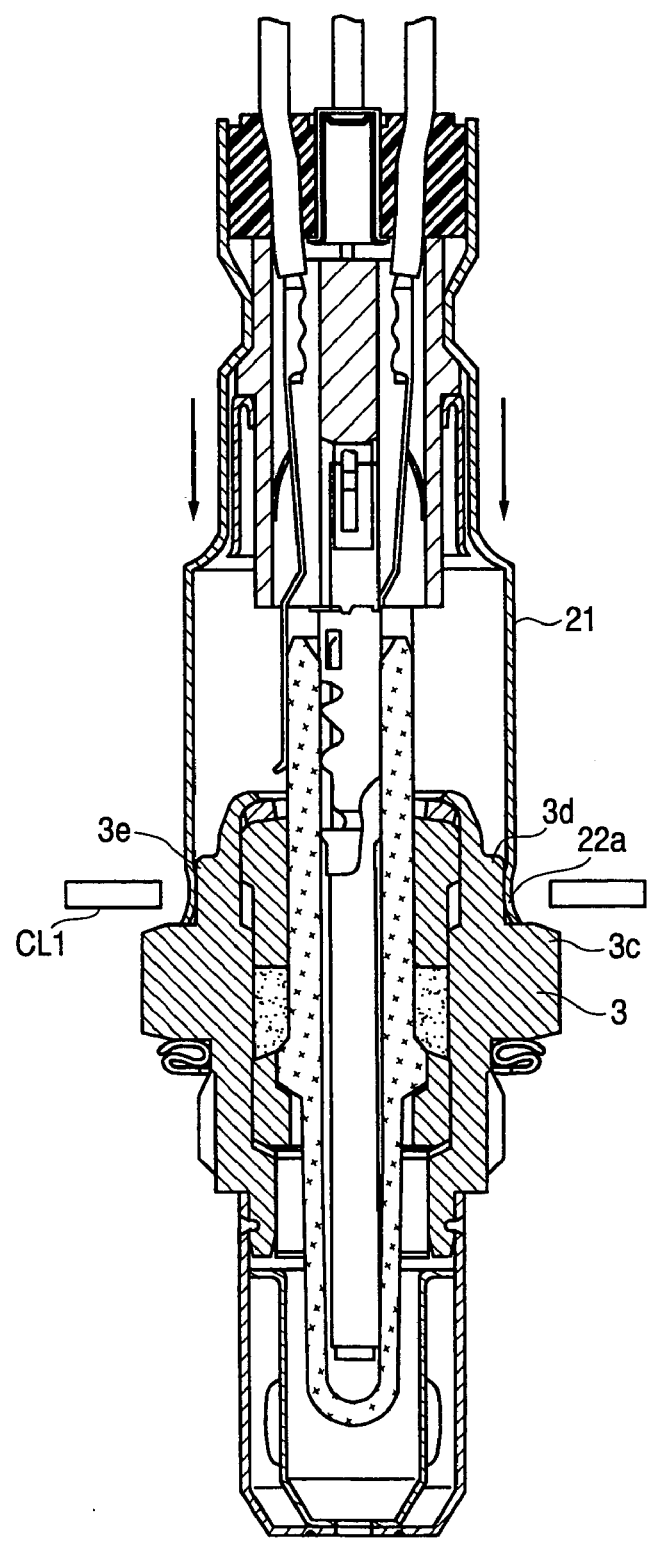
FIG. 10 is an explanatory view showing a manner of caulking the metal outer tube and a metal shell to provisionally connect them.

Thereafter, as shown in FIG. 10, a connecting portion 3e of the metal shell 3, and the tip end portion 22a of the metal outer tube 21 which is positioned on the outer peripheral side are caulked by a caulking jig CL1 to be provisionally connected, while pressing the metal outer tube 21 toward the tip end.

Figure 11:
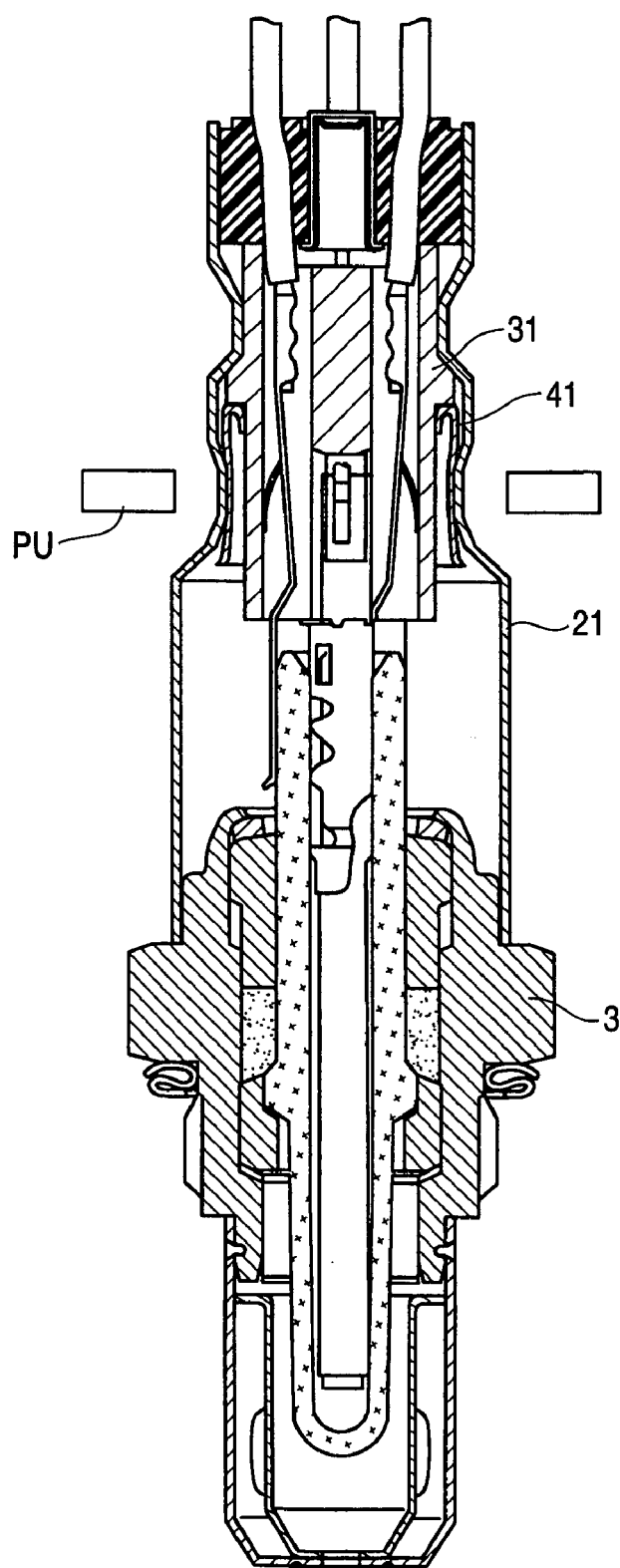
FIG. 11 is an explanatory view showing a deforming step of pressing the metal outer tube from the outer periphery to form a deformed portion, and deforming also the pressing metal part.

As shown in FIGS. 11 and 12, in the deforming step, the metal outer tube 21 is deformed by using a pressing jig PU, and also the pressing metal part 41 which is positioned inside the metal outer tube is deformed, whereby the separator 31 is fixed to the inside of the metal outer tube 21. FIG. 12(a) shows states of the metal outer tube 21, the separator 31, and the pressing metal part 41 before deformation. As described above, in this state, the outer-tube butting face 34a forming the tapered face in the flange portion 34 of the separator 31, and the flange butting face 24b forming the inclined face in the inner projection 24 of the metal outer tube 21 butt against each other, and the butting portions 43a of the J-shaped elastic holding portions 43 of the pressing metal part 41 (the rear end portion 42b of the metal tube portion 42) butt against the tip end side face 34b of the flange portion 34.

In the deforming step, therefore, a part of a pressing metal part surrounding portion 23a in the second outer tube potion 23 of the metal outer tube 21 which is positioned outside the pressing metal part 41 is deformed. Specifically, a part of the pressing metal part surrounding portion 23a is pressed by using a pressing jig PU so as to reduce the diameter, whereby the deformed portion 23b is formed into an annular shape as shown in FIG. 12(b). In accordance with this, also a part of the metal tube portion 42 of the pressing metal part 41 is deformed so as to reduce the diameter, and a deformed portion 42a is formed. As a result, the deformed portion 23b of the metal outer tube 21 and the deformed portion 42a of the pressing metal part 41 are in close contact with each other, and the pressing metal part 41 is held and fixed to the metal outer tube 21.

When the deformed portion 42a is formed in the pressing metal part 41 in this way, the portion of the metal tube portion 42 which is on the side of the rear end (the upper portion in the figure) with respect to the deformed portion 42a is slightly moved toward the rear end. Therefore, the curved rear end portion 42b of the metal tube portion 42 presses the flange portion 34 of the separator 31 toward the rear end (the upper portion in the figure). As a result, the flange portion 34 is sandwiched between the metal tube portion and the flange butting face 24b, and the separator 31 is fixed to the metal outer tube 21. Moreover, the outer-tube butting face 34a of the flange portion 34 is pressed so as to be pressed against the flange butting face 24b of the metal outer tube 21. Even when the axis 31x of the separator 31 is deviated from the axis 21x of the metal outer tube 21 for any reason, therefore, the deforming step causes the separator 31 to be moved and fixed so that the axis 31x of the separator 31 coincides with the axis 21x of the metal outer tube 21.

Particularly, the pressing metal part 41 comprises the J-shaped elastic holding portions 43 and tube elongating portions 44. Therefore, the butting portion between the tip end side face 34b and the pressing metal part 41 (the J-shaped elastic holding portions 43 and tube elongating portions 44) is formed into an interrupted annular shape of a very small width. As compared with the case where such a butting portion extends into a wide annular shape, therefore, the butting portion has width and annularly extends, therefore, the posture of the separator 31 (for example, deviation of the axis 31x of the separator 31 with respect to the axis 21x of the metal outer tube 21, inclination of the axis 31x, and rotation) can be changed in a relatively easy manner.

Therefore, a phenomenon in which stresses due to positional deviation of the separator 31 are generated in the heater 15, the first and second sensor terminal metal parts 11, 12, and the heater terminal metal parts 16, 17 is eliminated or reduced also by the deforming step. As a result, the terminal metal parts and the heater can be prevented from being broken or damaged, and the resulting oxygen sensor 1 is highly reliable.

In the embodiment, the pressing metal part 41 is used. After the heater 15 is inserted into the bottomed hole 2a of the oxygen sensor element 2, the oxygen sensor element 2 and the first and second sensor terminal metal parts 11, 12 are electrically connected, and the metal outer tube 21 butts against the metal shell 3, therefore, the metal outer tube 21 is deformed to fix the separator 21.

In the case where the deforming step is first conducted and the butting step is then conducted, the butting step is conducted in the state where the separator 31 is already fixed to the metal outer tube 21. In the butting step, even when stresses are applied to the first and second sensor terminal metal parts 11, 12, the heater terminal metal parts 16, 17, the heater 15, and the like because of displacement deviation or deformation of the first and second sensor terminal metal parts 11, 12 and the heater terminal metal parts 16, 17 in the separator 31, therefore, the separator 31 is fixed and hence cannot be adequately moved. Consequently, defects such as that the first and second sensor terminal metal parts 11, 12 are ruptured, that the heater 15 is bent, and that connections between the electrode pads 15e, 15f of the heater 15 and the heater terminal metal parts 16, 17 are broken may occur.

By contrast, in the configuration where the butting step is first conducted and the deforming step is then conducted as in the embodiment, even when stresses are applied to the first and second sensor terminal metal parts 11, 12, the heater terminal metal parts 16, 17, the heater 15, and the like in the butting step, the separator 31 in the loosely inserted state is adequately moved to eliminate or reduce the stresses. Therefore, a defect such as bending of the heater or rupture of the terminal metal parts hardly occurs.

Figure 13:
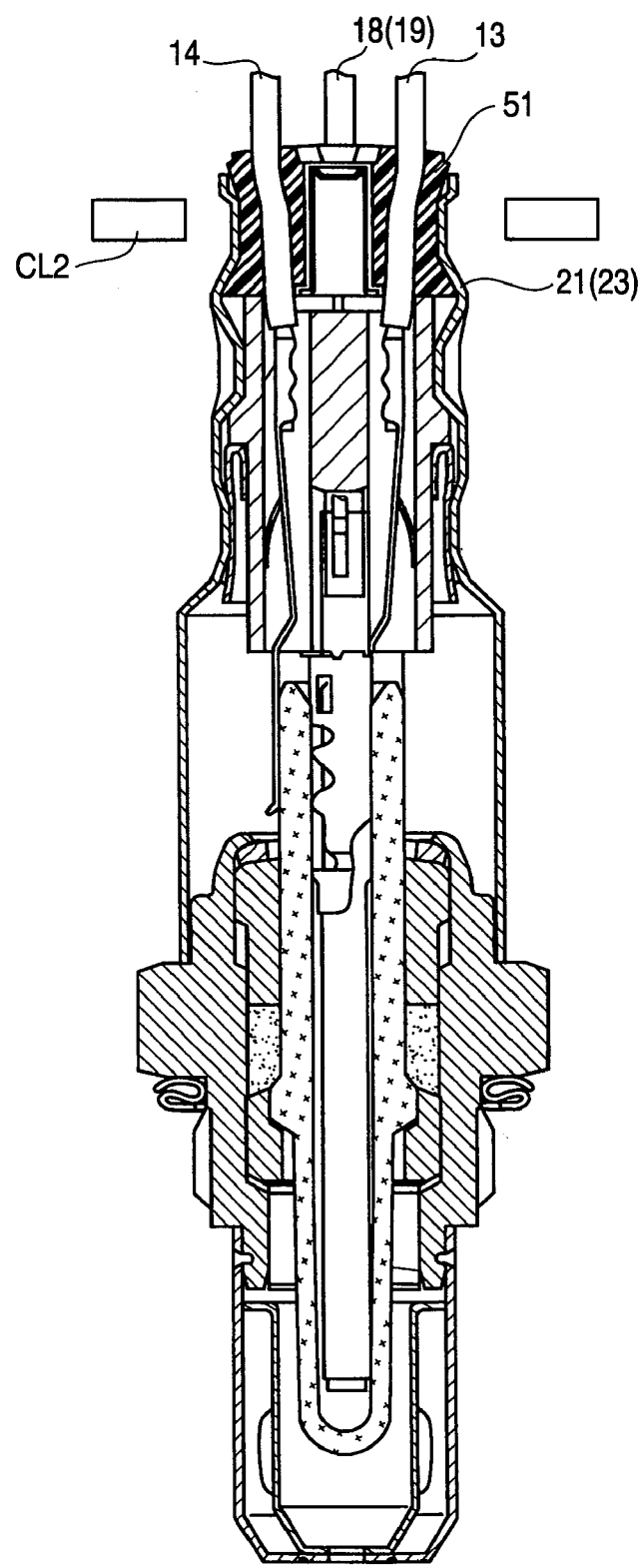
FIG. 13 is an explanatory view showing a manner of caulking a grommet.

Next, as shown in FIG. 13, the portion of the second outer tube potion 23 of the metal outer tube 21 which is positioned around the grommet 51 is caulked by a caulking jig CL2, so that the metal outer tube 21, the leas wire 13, and the like are airtightly sealed.

Figure 14:
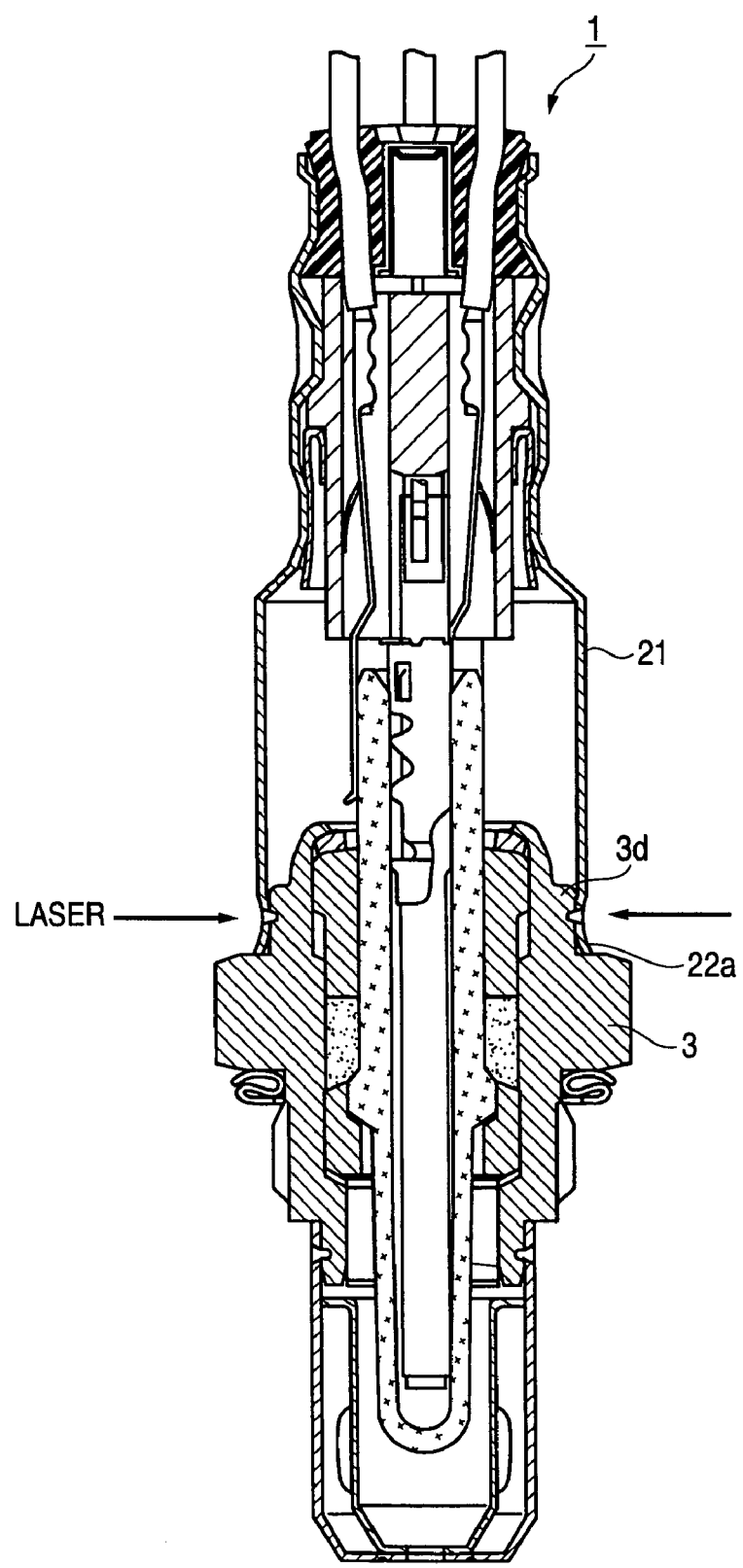
FIG. 14 is an explanatory view showing a manner of laser-welding the metal outer tube and the metal shell.

As shown in FIG. 14, the connecting portion 3d of the metal shell 3 and the tip end portion 22a of the metal outer tube 21 which are already provisionally connected to each other are airtightly connected by laser welding, thereby completing the oxygen sensor 1.

In the oxygen sensor 2 of the embodiment, as shown in FIG. 12(b), a gap is formed between the flange portion 34 of the separator 31 and a flange surrounding portion 23c of the metal outer tube 21 which is positioned around the flange portion 34. The outer diameter d2 (=14 mmφ) of the metal tube portion 42 of the pressing metal part 41 is slightly larger than the outer diameter d1 (=13.4 mmφ) of the flange portion 34. In the case where the oxygen sensor 1 is mounted on an automobile to be used, even when flying stone strikes against the flange surrounding portion 23c of the metal outer tube 21 and the metal outer tube 21 is largely depressed, therefore, the depressed metal outer tube 21 first collides with the metal tube portion 42 of the pressing metal part 41 before it collides with the flange portion 34 made of ceramic. Therefore, the collision is buffered, and a defect that the separator 31 is broken or cracked as a result of the hit of stone against the portion can be prevented from occurring.

In the above, the invention has been described by way of the embodiment. However, the invention is not restricted to the embodiment. It is a matter of course that the invention can be applied while being adequately modified without departing from the spirit of the invention.

For example, the embodiment in which the inner projection 24 is disposed in the four places in the circumferential direction of the metal outer tube 21 has been described. It is only necessary to dispose the inner projection in three places. By contrast, a step portion may be disposed so that an inclined face is formed over the whole of the metal outer tube in the circumferential direction.

In the embodiment described above, the pressing metal part 41 has a configuration in which the J-shaped elastic holding portion 43 is formed in the four places in the circumferential direction of the rear end of the metal tube portion 42. It is requested to form the J-shaped elastic holding portion in three or more places at regular intervals. Alternatively, a pressing metal part may be used which, in place of the J-shaped elastic holding portion, has an L-shaped elastic holding portion that elongates radially inward from the rear end of the metal tube portion 42, and that is then bent to elongate toward the tip end. Alternatively, in place of the pressing metal part, a cylindrical rubber member having an inner diameter which is smaller than the outer diameter of the tip end side portion 33 of the separator 31, and an outer diameter which, when the member is attached to the tip end side portion 33, is smaller than the inner diameter of the metal outer tube 21 may be used. When the cylindrical rubber member is used, in accordance with the formation of the deformed portion 23b of the metal outer tube 21 in the deforming step, the member is deformed to press the tip end side face 34b of the flange portion 34 of the separator 31 toward the rear end. When the cylindrical rubber member is used, the handling is facilitated.

Alternatively, the elastic member 1006 which is used in the above-described conventional art may be used. In this case also, when the outer-tube butting face 34a in which the diameter is made larger as further advancing toward the tip end side is disposed in the separator 31, and the flange butting face 24b forming an inclined face which is more radially outward positioned as further advancing toward the tip end is in the metal outer tube 21, it is possible to attain the effect that, when the separator 31 is to be fixed to the metal outer tube 21, the axis 31x of the separator 31 can be moved so as to coincide with the axis 21x of the metal outer tube 21 (see FIG. 9).

In the embodiment, the oxygen sensor 1 has been described. The invention can be applied also to other gas sensors such as a NOx sensor and an HC sensor. In the embodiment described above, the sensor element having a shape in which the tip end is closed is used as the oxygen sensor element 2. The shape can be adequately changed in accordance with the object to be detected. For example, a plate-like sensor element may be used. Since it is requested only that the outer-tube butting face 34a can be formed in the separator 31 and the flange butting face 24b can be formed in the metal outer tube 21, the invention can be applied also to a sensor in which a heater is not used. In the embodiment, both of the outer-tube butting face 34a of the separator 31 and the flange butting face 24b of the metal outer tube 21 are formed as a tapered face in which the diameter is made larger as further advancing toward the tip end. Alternatively, while a tapered face in which the diameter is made larger as further advancing toward the tip end may be formed in one of the separator 31 and the metal outer tube 21, the other one may be caused to butt against the tapered face. According to the configuration, it is expected to attain an effect that the position of the separator 31 can be adequately determined with respect to the metal outer tube 21.

Although the invention has been described in detail and with reference to a particular embodiment, it will be obvious to those skilled in the art that various changes and modifications may be made without departing the spirit and scope of the invention.

The present application is based on a Japanese patent application (Application No. 2002-211687) filed Jul. 19, 2002, and its disclosure is incorporated herein by reference.

The invention claimed is:

1. A sensor comprising:
 a sensor element;
 a metal shell which holds said sensor element;
 one or more sensor terminal members which are electrically connected to said sensor element, and which elongate from said sensor element toward a rear end;
 a metal outer tube which is connected to said metal shell at a tip end portion of said metal outer tube itself; and
 an electrically insulative separator which is housed inside said metal outer tube, in which said sensor terminal members are positioned, and which provides at least one of insulation between said sensor terminal members, and insulation between said sensor terminal members and said metal outer tube, wherein
 said separator has: a rear end side portion; and a flange portion which is positioned on a tip end side with respect to said rear end side portion, and which is larger in diameter than said rear end side portion,
 said metal outer tube has a step portion or an inner projection which butts against said flange portion of said separator,
 at least one of an outer-tube butting face of said flange portion of said separator, and a flange butting face of said step portion or said inner projection of said metal outer tube forms an inclined face which is more radially outward positioned as further advancing toward said tip end, said outer-tube butting face butting against said step portion or said inner projection of said metal outer tube and being positioned on a side of said rear end, said flange butting face butting against said outer-tube butting face of said flange portion of said separator, and
 said separator is held by said metal outer tube in a state where said separator is pressed toward said rear end,
 wherein a gap is present between the flange portion of the separator and a flange surrounding portion of the metal outer tube which is positioned around the flange portion.

2. The sensor according to claim 1, wherein both of the outer-tube butting face of said flange portion of said separator, and the flange butting face of said step portion or said inner projection of said metal outer tube form an inclined face which is more radially outward positioned as further advancing toward said tip end.

3. The sensor according to claim 1, wherein
 said flange portion of said separator has a tip end side face facing said tip end side, and
 said sensor comprises a pressing member which is held inside said metal outer tube, and which butts against said tip end side face of said flange portion to press said separator toward said rear end, said pressing member being in point contact with said tip end side face as seen in a radial direction.

4. The sensor according to claim 1, wherein
 said sensor element is a cylindrical gas sensor element in which a tip end side is closed,
 said sensor has:
 a rod heater which is inserted into a bottomed hole of said gas sensor element; and
 one or more heater terminal members which are electrically connected to said heater, and said separator is a separator which provides insulation between said sensor terminal members and said heater terminal members.

5. The sensor according to claim 1, wherein said pressing member radially inward presses said separator.

6. A sensor comprising:
a sensor element;
a metal shell which holds said sensor element;
one or more sensor terminal members which are electrically connected to said sensor element, and which elongate from said sensor element toward a rear end;
a metal outer tube which is connected to said metal shell at a tip end portion of said metal outer tube itself; and
an electrically insulative separator which is housed inside said metal outer tube, in which said sensor terminal members are positioned, and which provides at least one of insulation between said sensor terminal members, and insulation between said sensor terminal members and said metal outer tube, wherein
said sensor has a pressing member which holds said separator while axially rearward pressing said separator against said metal outer tube,
said metal outer tube has a first reduced-diameter portion which radially inward protrudes, and which butts against said separator, and a second reduced-diameter portion which butts against said pressing member,
said separator has, between said first reduced-diameter portion and said second reduced-diameter portion, a flange portion which butts at a rear end side against said metal outer tube while butting at a tip end side against said pressing member, and
at least one of said first reduced-diameter portion of said metal outer tube and said flange portion of said separator butts against another one via an inclined face which is more radially outward positioned as further advancing toward said tip end.

7. The sensor according to claim 6, wherein said pressing member radially inward presses said separator.

8. A sensor comprising:
a sensor element;
a metal shell which holds said sensor element;
one or more sensor terminal members which are electrically connected to said sensor element, and which elongate from said sensor element toward a rear end;
a metal outer tube which is connected to said metal shell at a tip end portion of said metal outer tube itself; and
an electrically insulative separator which is housed inside said metal outer tube, in which said sensor terminal members are positioned, and which provides at least one of insulation between said sensor terminal members, and insulation between said sensor terminal members and said metal outer tube, wherein
said sensor has a pressing member which holds said separator while axially rearward pressing said separator against said metal outer tube,
said metal outer tube has a first reduced-diameter portion which radially inward protrudes, and which butts against said separator, and a second reduced-diameter portion which holds said pressing member while radially inward pressing said pressing member, and
said separator has, between said first reduced-diameter portion and said second reduced-diameter portion, a flange portion which butts at a rear end side against said metal outer tube while butting at a tip end side against said pressing member.

9. The sensor according to claim 8, wherein said pressing member radially inward presses said separator.

10. A method for producing a sensor,
said sensor comprising:
a sensor element;
a metal shell which holds said sensor element;
one or more sensor terminal members which are electrically connected to said sensor element, and which elongate from said sensor element toward a rear end;
a metal outer tube which is connected to said metal shell at a tip end portion of said metal outer tube itself; and
an electrically insulative separator which is housed inside said metal outer tube,
said separator including:
a rear end side portion which is positioned on a side of said rear end;
a tip end side portion which is positioned on a side of a tip end; and
a flange portion which is positioned at a middle between said rear end side portion and said tip end side portion, which is larger in diameter than said rear end side portion and said tip end side portion, and which has a tip end side face facing said tip end side between said flange portion and said tip end side portion, and a rear end side face facing said rear end side between said flange portion and said rear end side portion,
said sensor terminal members being positioned inside,
said separator providing at least one of insulation between said sensor terminal members, and insulation between said sensor terminal members and said metal outer tube,
said metal outer tube having a step portion or an inner projection which butts against said rear end side of said flange portion of said separator,
said sensor having a pressing member which presses said separator toward said rear end, wherein
said method comprises:
a butting step of, in a state where said sensor terminal members are positioned inside said separator, said pressing member is held by an outer periphery of said tip end side portion of said separator, and said flange portion of said separator and said step portion or said inner projection of said metal outer tube butt against each other, moving at least one of said metal outer tube and said metal shell in a direction along which said metal outer tube and said metal shell approach each other, thereby causing said tip end portion of said metal outer tube to butt against said metal shell; and
a deforming step of, in a state where said sensor terminal members are positioned inside, said flange portion of said separator in which said pressing member is held by said outer periphery of said tip end side portion, and said step portion or said inner projection of said metal outer tube butt against each other, and said pressing member butts against said tip end side face of said flange portion of said separator, radially inward pressing a portion of said metal outer tube to form a deformed portion which inward protrudes, said portion being positioned in a radially outer side of said pressing member, and deform also said pressing member so that said pressing member presses said separator toward said rear end.

11. The method for producing a sensor according to claim 10, wherein
said rear end side face of said flange portion of said separator forms an inclined face which is more radially outward positioned as further advancing toward said tip end, and said step portion or said inner projection of said metal outer tube has a flange butting face forming an inclined face which butts against said rear end side face of said separator, and which is more radially outward positioned as further advancing toward said tip end.

12. The method for producing a sensor according to claim 10, wherein
said pressing member has:
a metal tube portion having an inner diameter which is larger than an outer diameter of said tip end side portion of said separator, and an outer diameter which is smaller than an inner diameter of said metal outer tube; and
an elastic holding portion which, when said metal tube portion is attached to said tip end side portion of said separator, elastically butts against said tip end side portion of said separator inside said metal tube portion, to hold said metal tube portion to said separator, and
in accordance with the formation of said deformed portion of said metal outer tube in said deforming step, said tip end side face of said flange portion of said separator is pressed toward said rear end by said rear end of said metal tube portion.

13. The method for producing a sensor according to claim 12, wherein
said metal tube portion of said pressing member has a rear end portion which is curved inward or outward in a radial direction.

14. The method for producing a sensor according to claim 12, wherein
said elastic holding portion of said pressing member is
a J-shaped elastic holding portion which is positioned in said rear end of said metal tube portion, which elongates radially inward, and which is gradually changed in direction to elongate toward said tip end to be curved into a substantially J-like shape.

15. The method for producing a sensor according to claim 10, wherein
said sensor element is a cylindrical gas sensor element in which a tip end side is closed,
said sensor has:
a rod heater which is inserted into a bottomed hole of said gas sensor element; and
one or more heater terminal members which are electrically connected to said heater,
said separator holds insulation between said sensor terminal members and said heater terminal members,
said butting step is conducted in a manner that, in a state where said separator is loosely inserted into said metal outer tube, at least one of said metal outer tube and said metal shell is moved in a direction along which they approach each other, to cause said tip end portion of said metal outer tube to butt against said metal shell, and said heater is inserted into said gas sensor element held by said metal shell, and
said deforming step is conducted after said butting step.

16. The method for producing a sensor according to claim 15, wherein
said butting step includes an inserting and positioning step of positioning and inserting a tip end of said heater to be guided into a rear end opening of said gas sensor element, said tip end further protruding toward said tip end than said tip end portion of said metal outer tube.

17. The method for producing a sensor according to claim 16, wherein
said inserting and positioning step is conducted by
guiding a part of a portion of said heater which further protrudes toward said tip end than said tip end portion of said metal outer tube, by a chuck device, and adjusting a position of said tip end of said heater.

18. An assembly of a separator and a pressing member which is to be used in a sensor,
said sensor comprising:
a sensor element;
a metal shell which holds said sensor element;
one or more sensor terminal members which are electrically connected to said sensor element, and which elongate from said sensor element toward a rear end;
a metal outer tube which is connected to said metal shell at a tip end portion of said metal outer tube itself; and
an electrically insulative separator which is housed inside said metal outer tube,
said separator including:
a rear end side portion which is positioned on a side of said rear end;
a tip end side portion which is positioned on a side of a tip end; and
a flange portion which is positioned at a middle between said rear end side portion and said tip end side portion, which is larger in diameter than said rear end side portion and said tip end side portion, and which has a tip end side face facing said tip end side between said flange portion and said tip end side portion, and an outer-tube butting face facing said rear end side between said flange portion and said rear end side portion,
said sensor terminal members being positioned inside,
said separator providing at least one of insulation between said sensor terminal members, and insulation between said sensor terminal members and said metal outer tube,
said metal outer tube having a step portion or an inner projection which has a flange butting face butting against said outer-tube butting face of said flange portion of said separator,
said sensor having a pressing member which presses said separator toward said rear end, wherein
said pressing member has:
a metal tube portion having an inner diameter which is larger than an outer diameter of said tip end side portion of said separator, and an outer diameter which is smaller than an inner diameter of said metal outer tube; and
an elastic holding portion which is placed inside said metal tube portion,
said elastic holding portion elastically butts against said-tip end side portion of said separator, and said pressing member is held by said separator.

* * * * *